United States Patent [19]

Tanaka

[11] Patent Number: 4,949,370
[45] Date of Patent: Aug. 14, 1990

[54] DENTAL X-RAY IRRADIATION INDICATING DEVICE

[75] Inventor: Hiroyuki Tanaka, Yokohama, Japan

[73] Assignee: Nix Company Limited, Tokyo, Japan

[21] Appl. No.: 230,513

[22] Filed: Aug. 10, 1988

[30] Foreign Application Priority Data

| Sep. 16, 1987 | [JP] | Japan | 62-140137[U] |
| Sep. 30, 1987 | [JP] | Japan | 62-148207[U] |
| Jan. 14, 1988 | [JP] | Japan | 63-2561[U] |
| Jan. 25, 1988 | [JP] | Japan | 63-7130[U] |
| Mar. 4, 1988 | [JP] | Japan | 63-28125[U] |
| Mar. 29, 1988 | [JP] | Japan | 63-40441[U] |
| Apr. 1, 1988 | [JP] | Japan | 63-42917[U] |

[51] Int. Cl.⁵ ............................................. A61B 6/14
[52] U.S. Cl. .................................... 378/170; 378/168; 378/205
[58] Field of Search ........................ 378/168–170, 378/205

[56] References Cited

U.S. PATENT DOCUMENTS

| 1,923,669 | 8/1933 | Harrison | 378/170 |
| 2,034,049 | 3/1936 | Levy | 378/170 |
| 2,090,933 | 8/1937 | Bolin | 378/170 |
| 2,127,502 | 8/1938 | De Weal | 378/170 |
| 4,057,732 | 11/1977 | Klauser | 378/170 |
| 4,507,798 | 3/1985 | Welander | 378/168 |
| 4,554,676 | 11/1985 | Maldonado et al. | 378/170 |
| 4,707,847 | 11/1987 | Van Aken | 378/168 |
| 4,815,117 | 3/1989 | Waldo | 378/168 |

FOREIGN PATENT DOCUMENTS

| 119300 | 9/1984 | European Pat. Off. |
| 3006608 | 9/1980 | Fed. Rep. of Germany |

Primary Examiner—Janice A. Howell
Assistant Examiner—John C. Freeman
Attorney, Agent, or Firm—Wegner & Bretschneider

[57] ABSTRACT

A dental X-ray irradiation indicating device which permits accurate indication of a location to be X-rayed and also permits photographing of an image substantially with the exact size. The device comprises a supporting member, an arm means extending from the supporting member, and an indicating member mounted on the arm means by way of a mounting member, whereby the indicating member is positioned in an opposing relationship to an intra-oral X-ray film package which is held in a predetermined angular position in an oral cavity of a patient. When an intra-oral X-ray photograph is to be taken, an X-ray is irradiated with reference to the indicating member of the device.

32 Claims, 20 Drawing Sheets

FIG. 12(a)
FIG. 12(b)
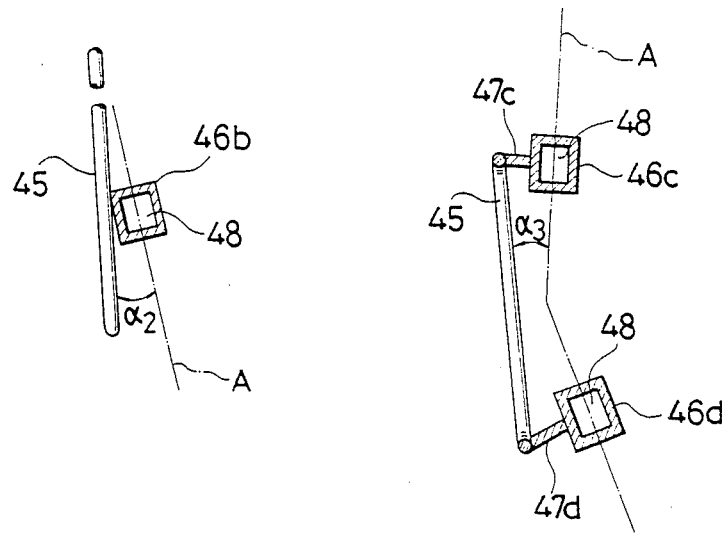
FIG. 13
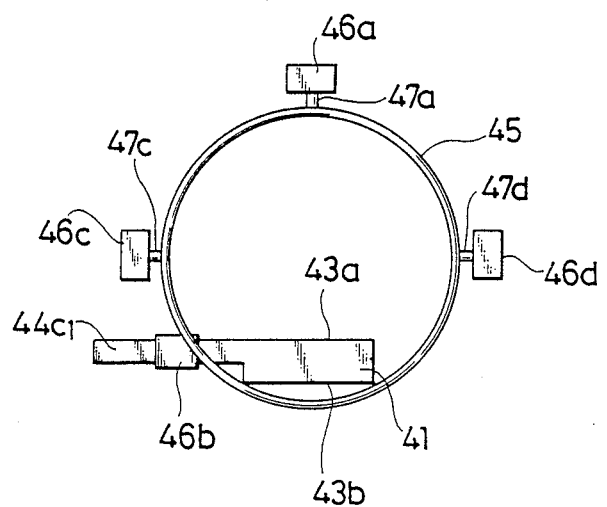

DENTAL X-RAY IRRADIATION INDICATING DEVICE

BACKGROUND OF THE INVENTION

1. Field of the Invention

This invention relates to a dental X-ray irradiation indicating device which is used for dental or intra-oral X-ray photographing.

2. Description of the Prior Art

When an X-ray photograph of a tooth is to be taken, a dental or intra-oral X-ray film package (hereinafter referred to only as film package) is positioned inside of the tooth (on the side adjacent the tongue) for an object of photographing, and an X-ray is irradiated upon the tooth from the outside. In such X-ray photographing, it is necessary to hold a film package at the specific position during photographing. A conventional supporting device for holding a film package in position is described below with reference to FIG. 1 which is a sectional view of an oral cavity in which the supporting device is used.

Referring to FIG. 1, reference symbol $1a$ and $1b$ denote each a tooth, $1a_1$ and $1b_1$ denote each an occlusal surface, 2 denote gums, 3 a tongue, and 4 a cheek. Reference numeral 5 denotes a supporting device adapted to be bitten between the teeth $1a$ and $1b$, and the supporting device 5 is made of a comparatively soft or flexible substance and has a shape of a parallelepiped having a rectangular cross section. Reference numeral 6 denotes a film package adhered to an end face of the supporting device 5, and 7 an X-ray film enclosed in the film package 6.

The supporting device 5 and the film package 6 are initially prepared independently of each other. In preparation for X-ray photographing, the supporting device 5 is adhered to a predetermined location of the film package 6, and then the film package 6 is inserted into the oral cavity and positioned at such a position as to allow an X-ray photograph of the tooth $1a$ to be taken. Then, the supporting device 5 is bitten between the teeth $1a$ and $1b$ so as to hold the film package 6 at the position. An X-ray is subsequently irradiated from the outside of the cheek 4 toward the tooth $1a$ as indicated by an arrow mark X. Consequently, an X-ray image (latent image) of the tooth $1a$ is produced on the X-ray film 7. The film package 6 is then taken out of the oral cavity, and the envelope or cover of the film package 6 is torn away to take out the X-ray film 7. The X-ray film 7 is then developed and fixed to produce a visible X-ray image of the tooth $1a$ on the X-ray film 7.

In such X-ray photographing as described above, however, it is not possible to accurately discriminate, from outside, the position of the X-ray film 7 and hence the position of the tooth $1a$ for an object of photographing, and it is quite impossible to discriminate the slope with which the X-ray film 7 is inclined by the gums contacting therewith. Accordingly, in conventional X-ray photographing, a photographer takes aim roughly at the position of the X-ray film 7 or the tooth $1a$ and directs an X-ray to the location. An X-ray image of the tooth $1a$ can be obtained even by such rough means because the X-ray diffuses to some degree. It is very troublesome, however, to take aim at the position of the X-ray film 7 or a tooth for an object of photographing from outside each time a photograph is to be taken. Besides, when the X-ray is stopped down in order to obtain a clearer X-ray image, mere taking aim may not permit accurate irradiation of the X-ray, and actually it is difficult to obtain a clear X-ray image. Further, normally the X-ray film 7 is inclined with respect to a vertical line interconnecting the upper and lower teeth $1a$ and $1b$ due to presence of the gums 2 as described above. In this instance, it is almost impossible to produce an image of the tooth $1a$ with the exact size on the X-ray film 7. There is the possibility, therefore, that the diagnosis and/or treatment depending upon the X-ray image may lack in accuracy.

SUMMARY OF THE INVENTION

It is an object of the present invention to provide a dental X-ray irradiation indicating device which permits accurate indication of a location to be X-rayed.

It is another object of the present invention to provide a dental X-ray irradiation indicating device which permits photographing of an image substantially with the exact size.

In order to attain the objects, according to one aspect of the present invention, there is provided a dental X-ray irradiation indicating device for holding an intra-oral X-ray film package in an oral cavity of a patient and for indicating a direction in which an X-ray is to be irradiated from outside the oral cavity, which comprises a supporting member having a film fixing portion to which an intra-oral X-ray film package is to be fixed and a bitten portion adapted to be bitten by a tooth, an arm means which extends outwardly of an oral cavity from the supporting member when the bitten portion of the supporting member is bitten by a tooth, an indexing means for indicating a direction in which an X-ray is to be irradiated, the indexing means including a first indexing element defining a first plane, a second indexing element defining a second plane which is inclined by a predetermined angle with respect to the first plane, and a connecting element for interconnecting the first and second indexing elements, and a mounting structure for removably mounting the indexing means on the arm means. With the dental X-ray irradiation indicating device, the first indexing element or the second indexing element is selectively used depending upon the position of a tooth to be photographed. An X-ray is thus irradiated with reference to the first or second plane of the thus selected first or second indexing element. Consequently, an X-ray image is produced with the substantially exact size on an X-ray film.

According to another aspect of the present invention, there is provided a dental X-ray irradiation indicating device for holding an intra-oral X-ray film package in an oral cavity of a patient and for indicating a direction in which an X-ray is to be irradiated from outside the oral cavity, which comprises a supporting member having a film fixing portion to which an intra-oral X-ray film package is to be fixed and a bitten portion adapted to be bitten by a tooth, an arm means which extends outwardly of an oral cavity from the supporting member when the bitten portion of the supporting member is bitten by a tooth, an indexing element for indicating a direction in which an X-ray is to be irradiated, and a mounting structure provided on the indexing element for removably mounting the indexing element at a different angular position on the arm means. With the dental X-ray irradiation indicating device, the indexing element is mounted on the arm means by the mounting structure such that it may be inclined by an angle depending upon the position of a tooth to be photographed, and an X-ray is irradiated in a direction perpendicular to the thus inclined plane of the indexing element. Consequently, an X-ray image is produced with the substantially exact size on an X-ray film.

According to a further aspect of the present invention, there is provided a dental X-ray irradiation indicating device for holding an intra-oral X-ray film package in an oral cavity of a patient and for indicating a direction in which an X-ray is to be irradiated from outside the oral cavity, which comprises a supporting member having a film fixing portion to which an intra-oral X-ray film package is to be fixed and a bitten portion adapted to be bitten by a tooth, an arm means which extends outwardly of an oral cavity from the supporting member when the bitten portion of the supporting member is bitten by a tooth, and an indexing element for indicating a direction in which an X-ray is to be irradiated, the indexing element having a single mounting member at which the indexing element is to be mounted on the arm means, the indexing element being disposed in a predetermined angular position with respect to a plane of the intra-oral X-ray film package held in position in the oral cavity. With the dental X-ray irradiation indicating device, the mounting member of the indexing element is mounted on the arm means, and an X-ray is irradiated in a direction perpendicular to the plane of the indexing element. Consequently, an X-ray image is produced with the substantially exact size on an X-ray film.

According to a still further aspect of the present invention, there is provided a dental X-ray irradiation indicating device for holding an intra-oral X-ray film package in an oral cavity of a patient and for indicating a direction in which an X-ray is to be irradiated from outside the oral cavity, which comprises a supporting member having a film fixing portion to which an intra-oral X-ray film package is to be fixed and a bitten portion adapted to be bitten by a tooth, an arm means which extends outwardly of an oral cavity from the supporting member when the bitten portion of the supporting member is bitten by a tooth, an extension extending from an end of the arm means, and an indexing element provided at an end of the extension for indicating a direction in which an X-ray is to be irradiated, the indexing element being disposed in a predetermined angular position with respect to a plane of the intra-oral X-ray film package held in position in the oral cavity, whereby the supporting member, arm means, extension and indexing element are formed as a unitary member. With the dental X-ray irradiation indicating device, an X-ray is irradiated taking aim at the indexing element. Consequently, an X-ray image is produced with the substantially exact size on an X-ray film.

According to a yet further aspect of the present invention, there is provided a dental X-ray irradiation indicating device for holding an intra-oral X-ray film package in an oral cavity of a patient and for indicating a direction in which an X-ray is to be irradiated from outside the oral cavity, which comprises a supporting member having a fixing portion and a bitten portion adapted to be bitten by a tooth, an arm means having a first face adapted to be fixed to the fixing portion of the supporting member, a second face to which an intra-oral X-ray film is to be fixed, and an arm portion which extends outwardly of an oral cavity when the first face of the arm means is fixed to the fixing portion of the supporting member and the bitten portion of the supporting member is bitten by a tooth, a mounting element provided on the arm means, and an indexing element mounted on the mounting element for indicating a direction in which an X-ray is to be irradiated, the indexing element being disposed in a predetermined angular position with respect to a plane of the intra-oral X-ray film package held in position in the oral cavity. With the dental X-ray irradiation indicating device, an X-ray is irradiated in a direction perpendicular to the plane of the indexing element. Consequently, an X-ray image is produced with the substantially exact size on an X-ray film.

According to a yet further aspect of the present invention, there is provided a dental X-ray irradiation indicating device for holding an intra-oral X-ray film package in an oral cavity of a patient and for indicating a direction in which an X-ray is to be irradiated from outside the oral cavity, which comprises a supporting member having an adhering portion to which a layer of a bonding agent is applied and a bitten portion adapted to be bitten by a tooth, an arm means which extends outwardly of an oral cavity from the supporting member when the bitten portion is held in position in the oral cavity, an indexing element removably mounted at a predetermined location on the arm means for indicating a direction in which an X-ray is to be irradiated, the indexing element being disposed in a predetermined angular position with respect to a plane of an intra-oral X-ray film package held in position in the oral cavity, and a support element having an adhering face adapted to be adhered to the adhering portion of the supporting member and a supporting portion for supporting an intra-oral X-ray film package thereon. With the dental X-ray irradiation indicating device, an X-ray is irradiated in a direction perpendicular to the plane of the indexing element. Consequently, an X-ray image is produced with the substantially exact size on an X-ray film.

The above and other objects, features and advantages of the present invention will become apparent from the following description and the appended claims, taken in conjunction with the accompanying drawings.

BREIF DESCRIPTION OF THE DRAWINGS

Figure 1:
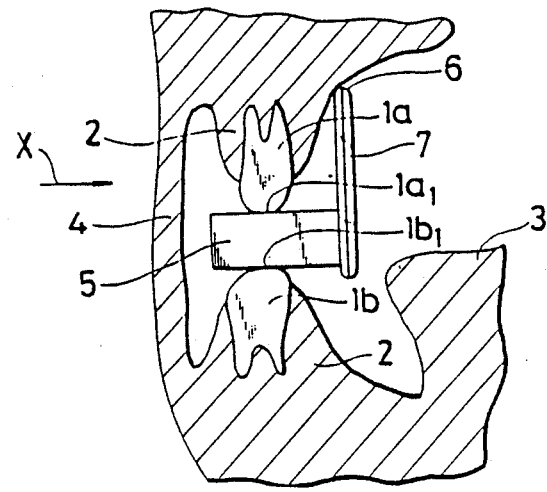
FIG. 1 is a sectional view of part of an oral cavity in which a conventional supporting device is used.
Figure 2:
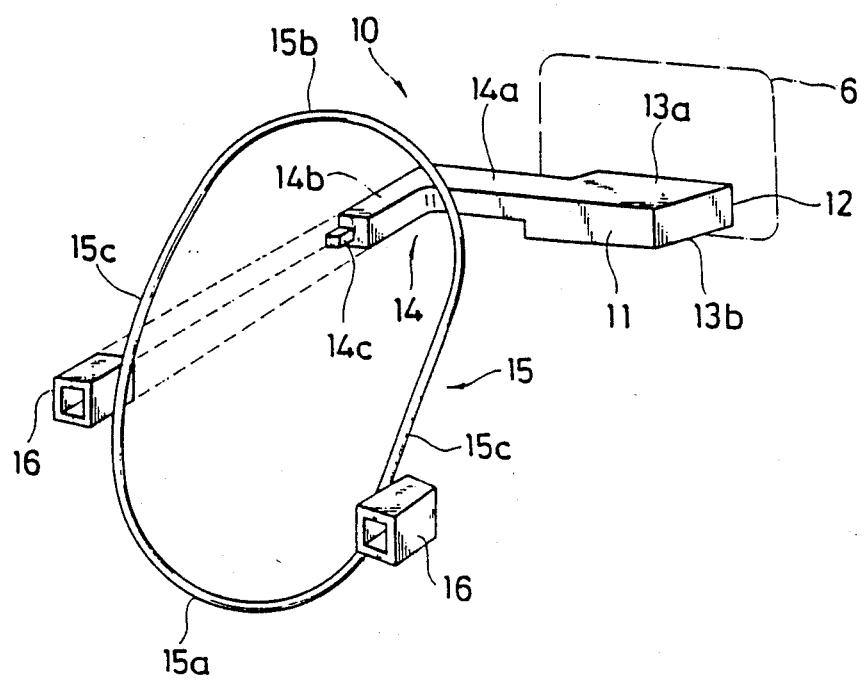
FIG. 2 is a fragmentary perspective view of a dental X-ray irradiation indicating device showing a first embodiment of the present invention.
Figure 3A:
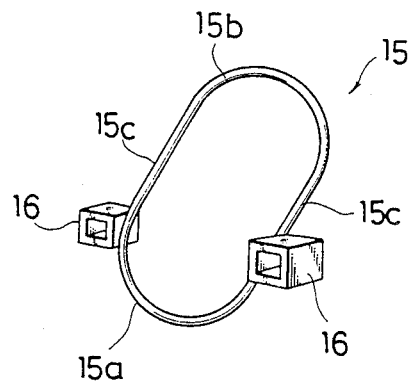
Figure 3B:
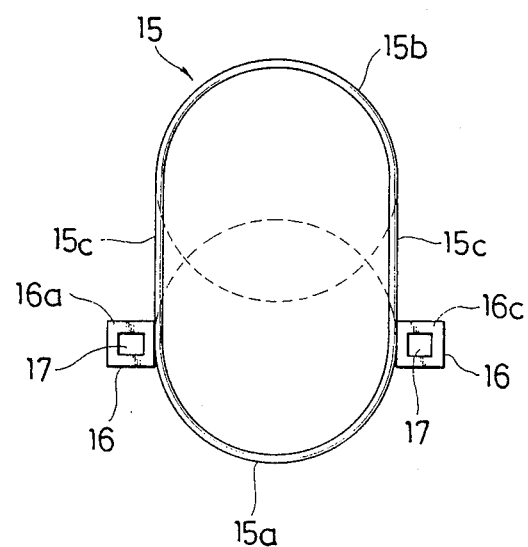
Figure 3C:
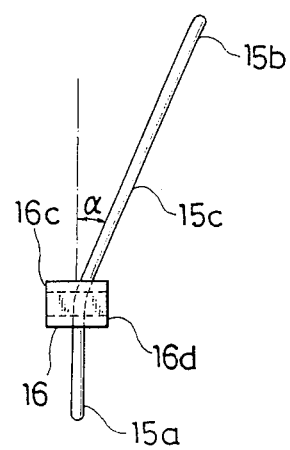
Figure 4:
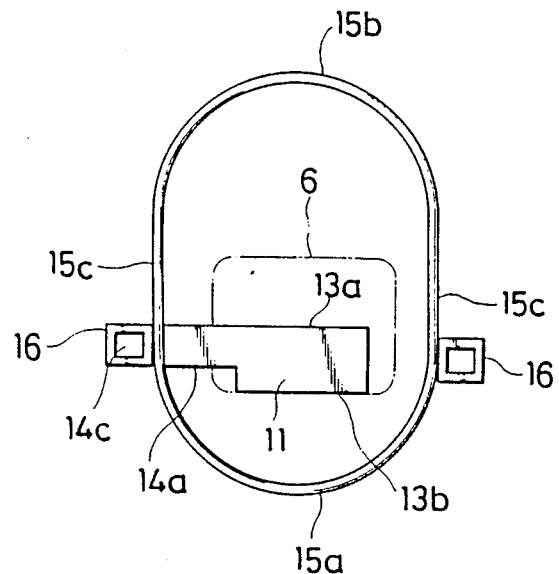
Figure 5A:
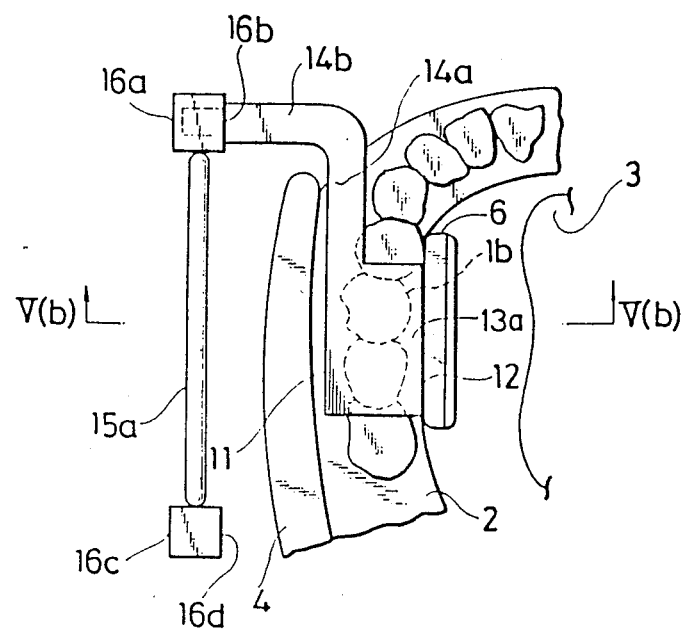
Figure 5B:
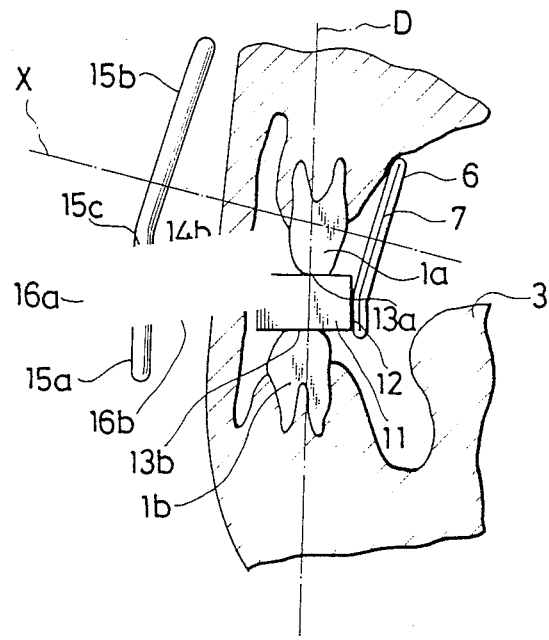
Figure 6A:
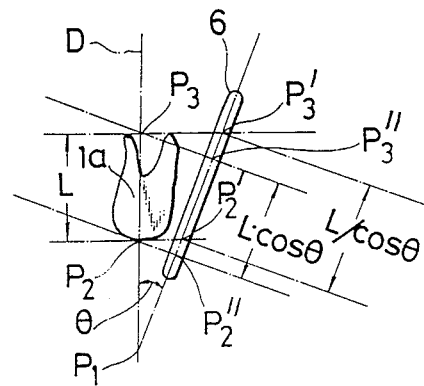
Figure 6B:
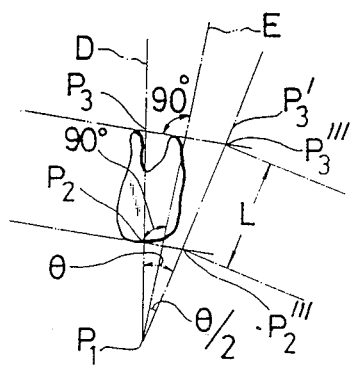
Figure 7A:
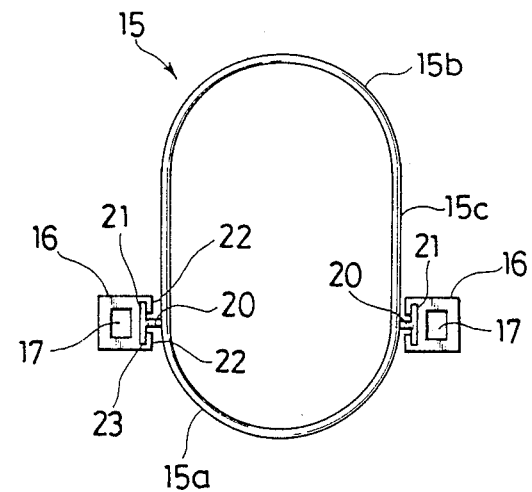
Figure 7B:
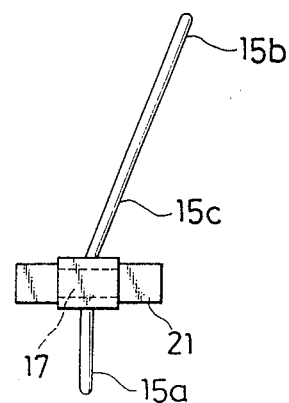
Figure 8A:
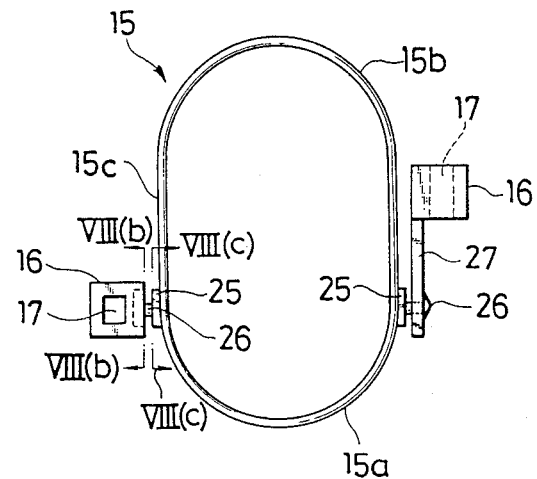
Figure 8B:
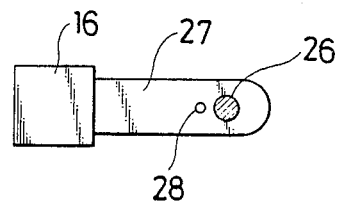
Figure 8C:
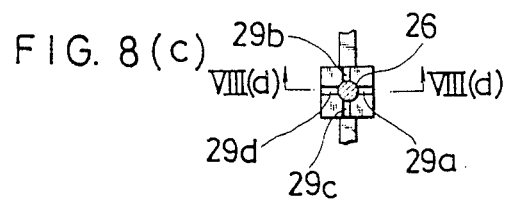
Figure 8D:
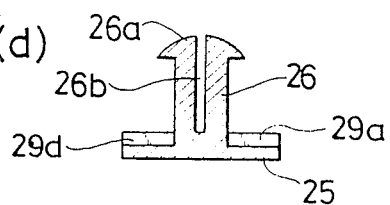
Figure 9A:
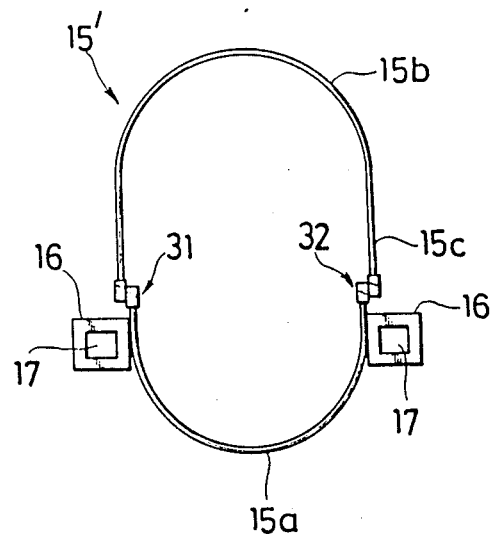
Figure 9B:
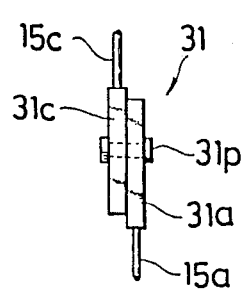
Figure 9C:
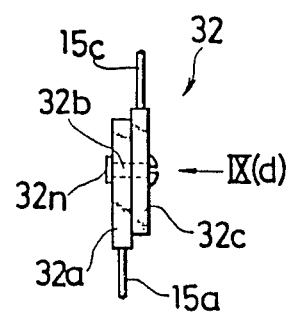
Figure 9D:
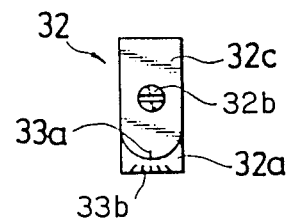
Figure 10:
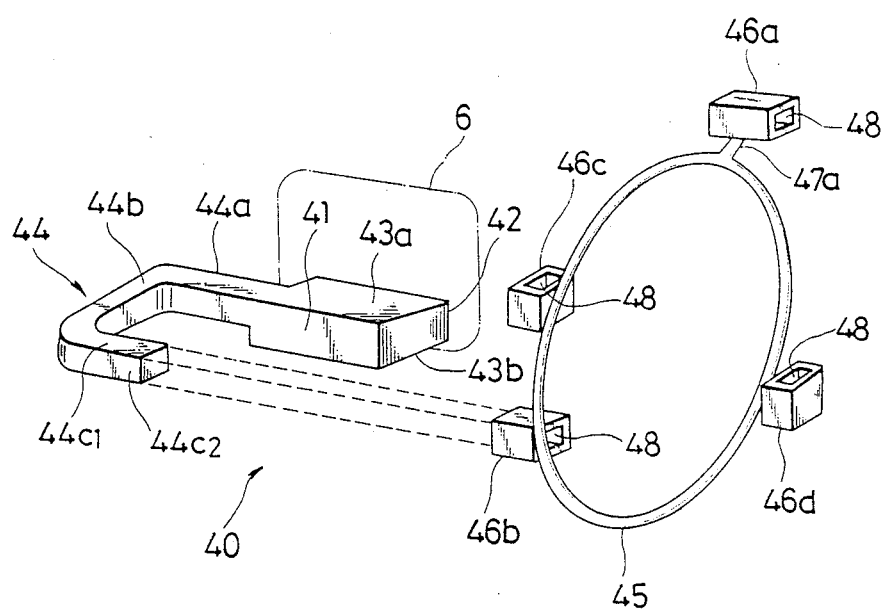
Figure 11:
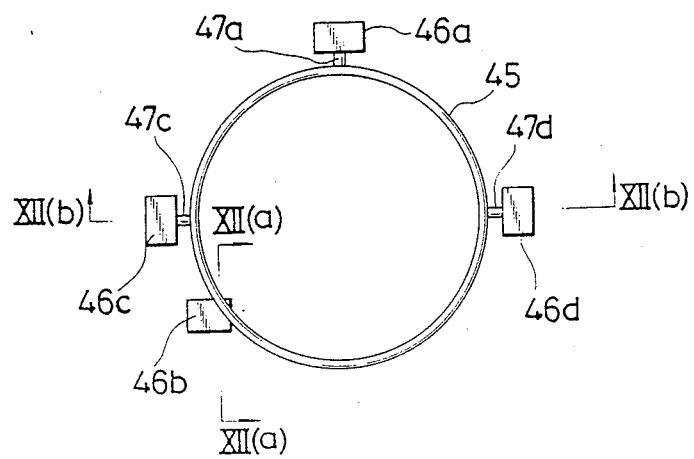
Figure 14A:
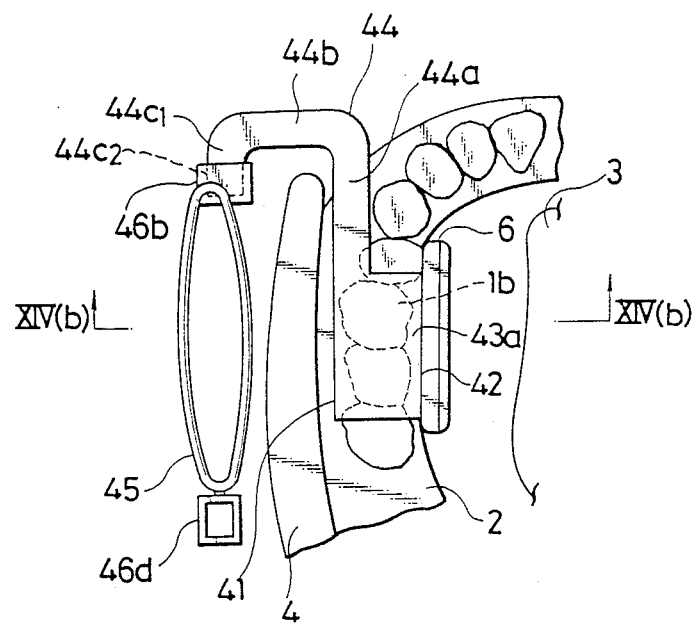
Figure 14B:
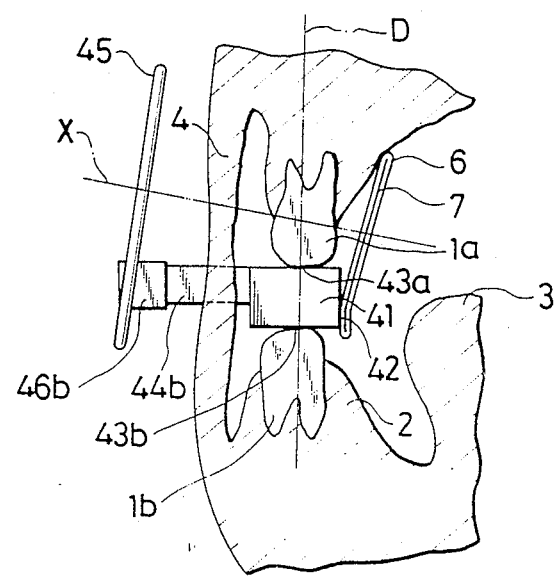
Figure 15A:
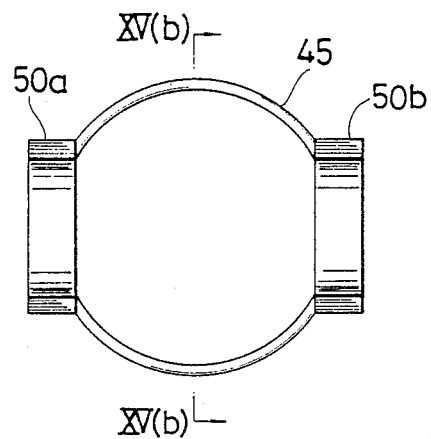
Figure 15B:
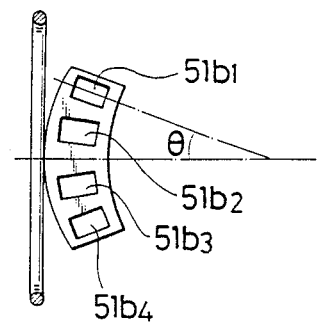
Figure 16A:
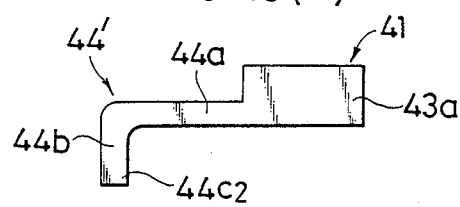
Figure 16B:
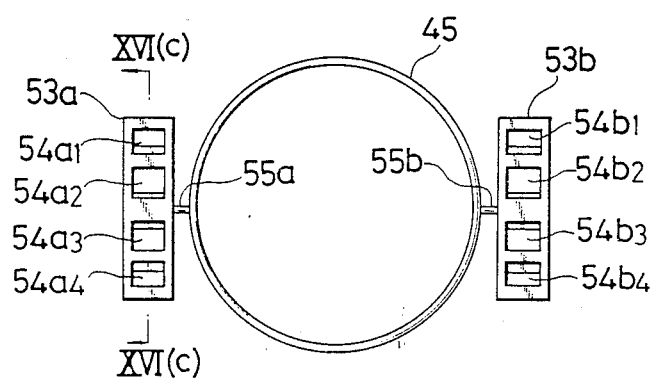
Figure 16C:
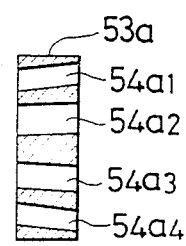
Figure 17A:
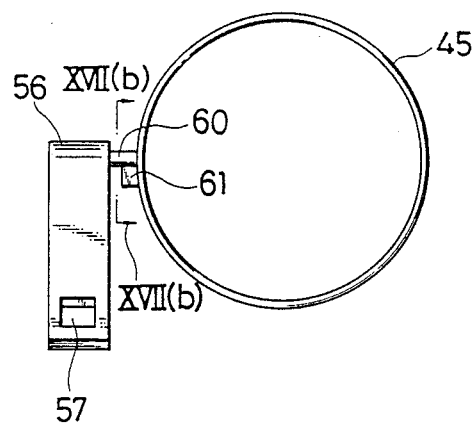
Figure 17B:
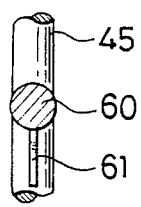
Figure 17C:
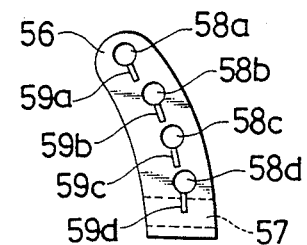
Figure 18:
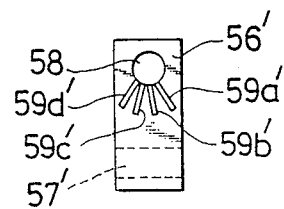
Figure 19A:
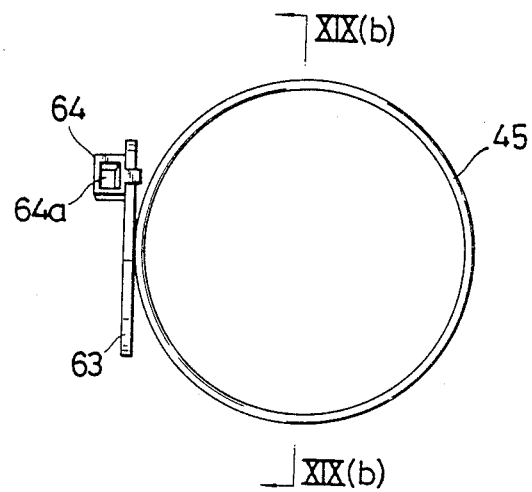
Figure 19B:
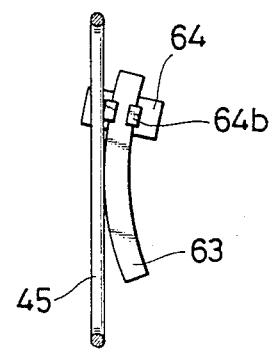
Figure 20A:
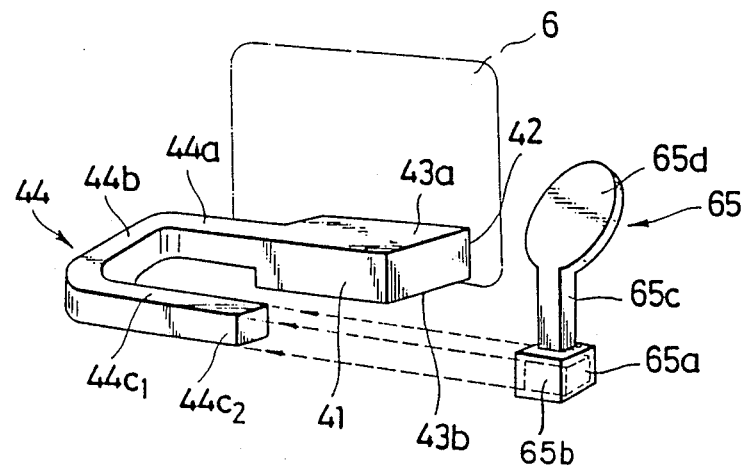
Figure 20B:
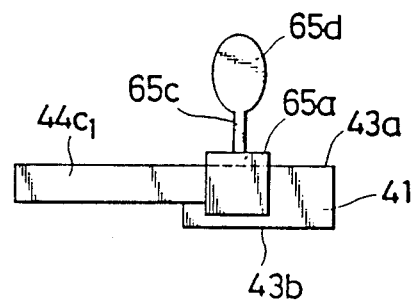
Figure 21A:
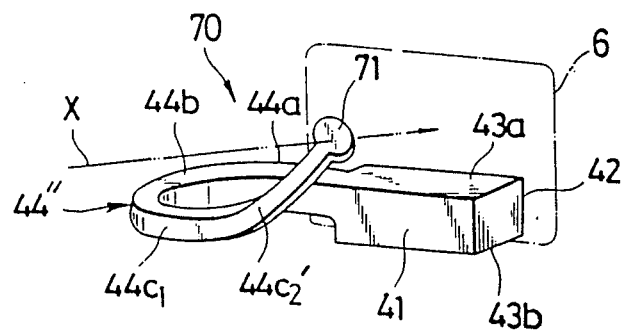
Figure 21B:
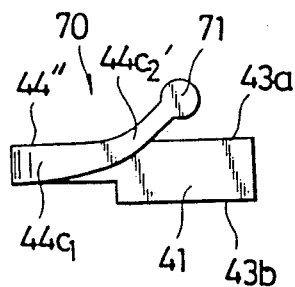
Figure 22:
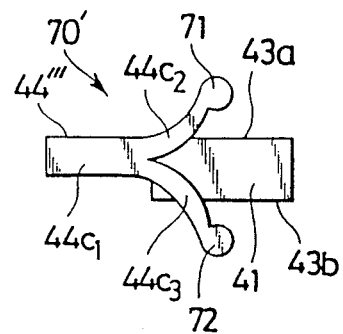
Figure 23A:
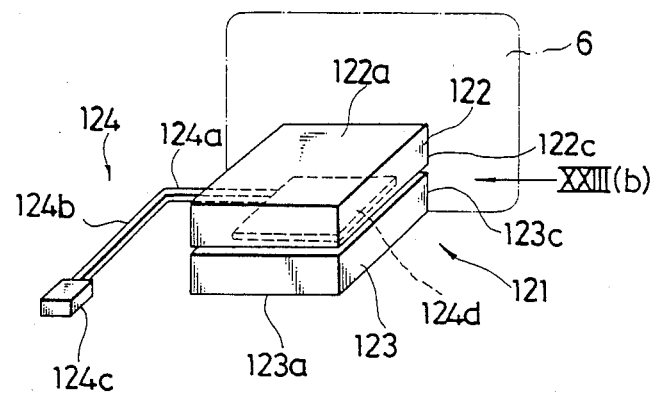
Figure 23B:
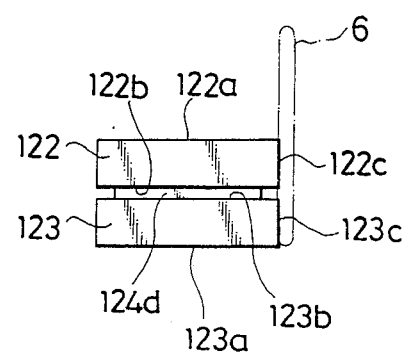
Figure 24:
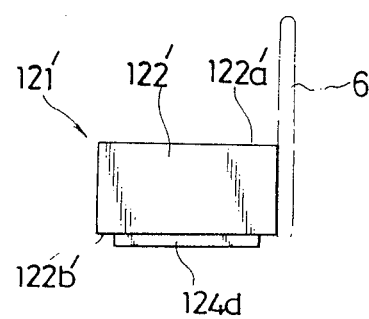
Figure 25:
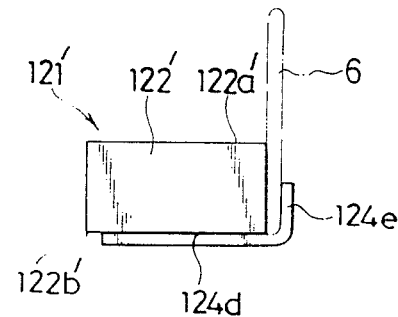
Figure 26A:
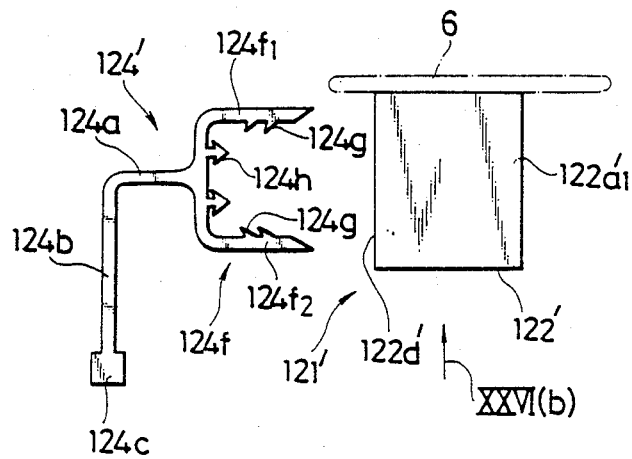
Figure 26B:
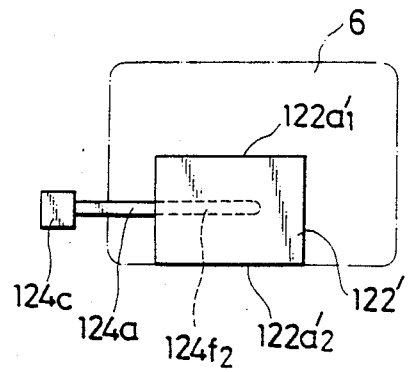
Figure 27:
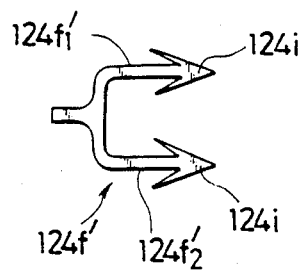
Figure 28:
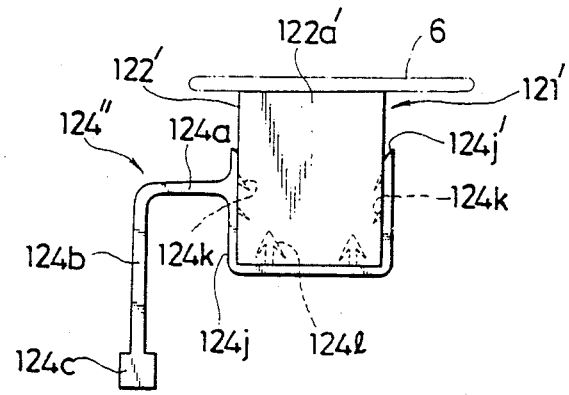
Figure 29A:
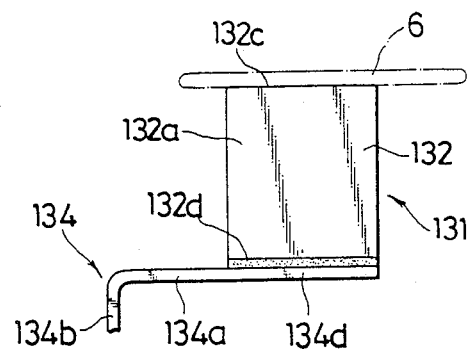
Figure 29B:
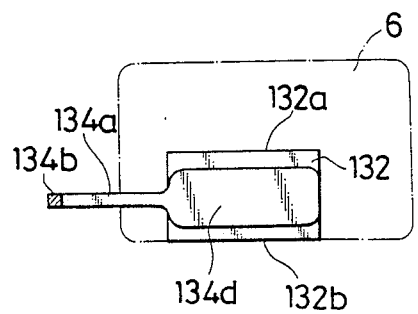
Figure 32:
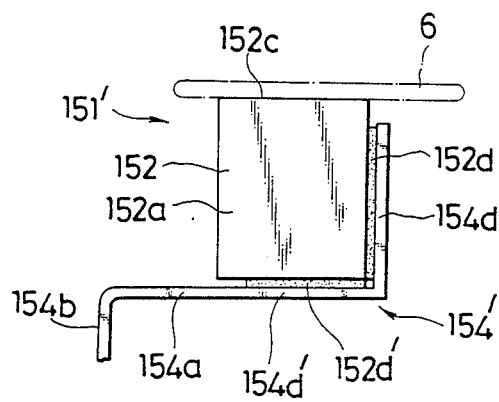
Figure 33:
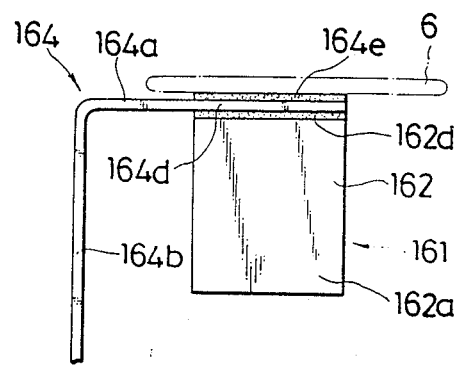
Figure 34A:
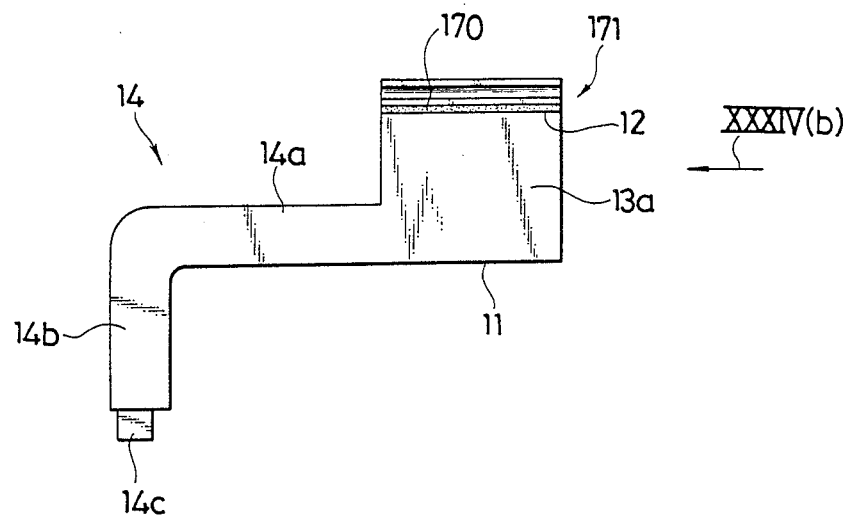
Figure 34B:
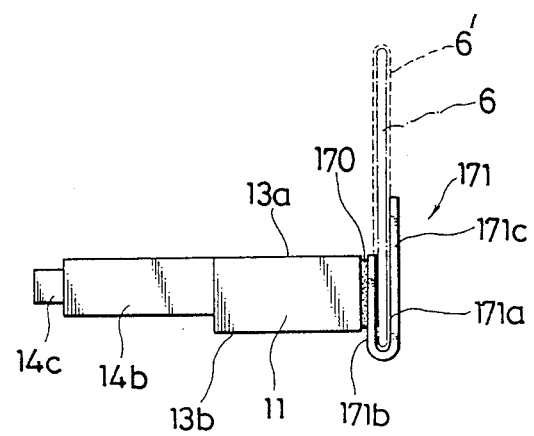

FIGS. 3(a), 3(b) and 3(c) are a perspective view, a front elevational view and a side elevational view, respectively, of an indicating member of the device shown in FIG. 2;

FIG. 4 is a front elevational view of the dental X-ray irradiation indicating device shown in FIG. 2 on which the indicating member shown in FIGS. 3(a), 3(b) and 3(c) is mounted;

FIG. 5(a) is a plan view of part of an oral cavity upon photographing of a tooth using the dental X-ray irradiation indicating device of FIG. 2, and FIG. 5(b) is a sectional view taken along line Vb—Vb of FIG. 5(a);

FIGS. 6(a) and 6(b) are diagrammatic representations illustrating an inclination of the indicating member shown in FIGS. 3(a) to 3(c);

FIGS. 7(a) and 7(b) are a front elevational view and a side elevational view, respectively, of an indicating member and a mounting structure for the same of a dental X-ray irradiation indicating device showing a second embodiment of the present invention;

FIG. 8(a) is a front elevational view of an indicating member and a mounting structure for the same of a dental X-ray irradiation indicating device showing a third embodiment of the present invention, and FIGS. 8(b) and 8(c) are enlarged sectional views taken along line VIIIb—VIIIb and line VIIIc—VIIIc of FIG. 8(a), respectively, and FIG. 8(d) is an enlarged sectional view taken along line VIIId—VIIId of FIG. 8(c);

FIG. 9(a) is a front elevational view of an indicating member and a mounting structure for the same of a dental X-ray irradiation indicating device showing a fourth embodiment of the present invention, and FIGS. 9(b) and 9(c) are enlarged front elevational views of pivotally connecting portions of the indicating member shown in FIG. 9(a) and FIG. 9(d) is a side elevational view of the pivotally connecting portion shown in FIG. 9(c);

FIG. 10 is a fragmentary perspective view of a dental X-ray irradiation indicating device showing a fifth embodiment of the present invention;

FIG. 11 is a front elevational view of a ring and mounting members of the device shown in FIG. 10;

FIGS. 12(a) and 12(b) are sectional views, in an enlarged scale, taken along line XIIa—XIIa and line XIIb—XIIb of FIG. 11, respectively;

FIG. 13 is a front elevational view showing the ring mounted on an arm of the device of FIG. 10;

FIG. 14(a) is a plan view of part of an oral cavity upon photographing of a tooth using the dental X-ray irradiation indicating device of FIG. 10, and FIG. 14(b) is a sectional view taken along line XIVb—XIVb of FIG. 14(a);

FIGS. 15(a) and 15(b) are a front elevational view and a sectional view taken along line XVb—XVb of FIG. 15(a), respectively, of a ring and a mounting block of a dental X-ray irradiation indicating device showing a sixth embodiment of the present invention;

FIGS. 16(a) and 16(b) are a plan view of an arm and a front elevational view of a ring and a mounting block, respectively, of a dental X-ray irradiation indicating device showing a seventh embodiment of the present invention, and FIG. 16(c) is a sectional view taken along line XVIc—XVIc of FIG. 16(b);

FIG. 17(a) is a front elevational view of a ring and a mounting block of a dental X-ray irradiation indicating device showing an eighth embodiment of the present invention, and FIG. 17(b) is an enlarged sectional view taken along line XVIIb—XVIIb of FIG. 17(a) and FIG. 17(c) is a side elevational view of the mounting block shown in FIG. 17(a);

FIG. 18 is a side elevational view of a mounting block of a dental X-ray irradiation indicating device showing a ninth embodiment of the present invention;

FIG. 19(a) is a front elevational view of a ring and a mounting structure for the same of a dental X-ray irradiation indicating device showing a tenth embodiment of the present invention, and FIG. 19(b) is a sectional view taken along line XIXb—XIXb of FIG. 19(a);

FIGS. 20(a) and 20(b) are a fragmentary perspective view and a side elevational view, respectively, of a dental X-ray irradiation indicating device showing an eleventh embodiment of the present invention;

FIGS. 21(a) and 21(b) are a perspective view and a side elevational view, respectively, of a dental X-ray irradiation indicating device showing a twelfth embodiment of the present invention;

FIG. 22 is a side elevational view of a dental X-ray irradiation indicating device showing a thirteenth embodiment of the present invention;

FIGS. 23(a) and 23(b) are a perspective view and a side elevational view, respectively, showing a first example of coupling structure between a supporting member and an arm;

FIGS. 24 and 25 are side elevational views showing second and third examples, respectively, of coupling structure between a supporting member and an arm;

FIGS. 26(a) and 26(b) are a fragmentary plan view and a side elevational view, respectively, showing of a fourth example of coupling structure between a supporting member and an arm;

FIG. 27 is a plan view of a piercing portion of an arm showing a fifth example of coupling structure between a supporting member and the arm;

FIG. 28 is a plan view showing a sixth example of coupling structure between a supporting member and an arm;

FIGS. 29(a) and 29(b) are a plan view and a side elevational view, respectively, showing a seventh example of coupling structure between a supporting member and an arm;

FIGS. 30, 31, 32 and 33 are plan views showing eighth, ninth, tenth and eleventh examples, respectively, of coupling structure between a supporting member and an arm; and FIG. 34(a) is a plan view of a supporting structure for a film package, and FIG. 34(b) is a side elevational view as viewed in the direction of an arrow mark XXXIVb in FIG. 34(a).

DESCRIPTION OF THE PREFERRED EMBODIMENTS

Referring first to FIGS. 2 to 4, there is shown a dental X-ray irradiation indicating device according to a first embodiment of the present invention. The dental X-ray irradiation indicating device is generally denoted at 10 and includes a supporting member 11 in the form of a parallelepiped having a rectangular cross section and made of a comparatively soft material such as, for example, foamed polyethylene, sponge or rubber. The supporting member 11 has an adhering portion or face 12 for adhering a film package thereto. A bonding agent is applied to the adhering portion 12 of the supporting member 11 in advance, and when an X-ray photograph is to be taken, a film package 6 is adhered to the adhering portion 12 as shown in phantom in FIGS. 2 and 4. The supporting member 11 further has a pair of upper and lower bitten faces or portions 13a and 13b adapted to be bitten by upper and lower opposing teeth when an X-ray photograph is to be taken.

An arm 14 having a substantially L-shape in plan extends from the supporting member 11. The arm 14 has a portion 14a extending laterally from an end of the supporting member 11 and having a face in the common plane with a face of the supporting member 11 opposite the adhering face or portion 12, another portion 14b contiguous to the portion 14a and extending in a direction substantially perpendicular to the portion 14a, and a mounting portion 14c at the other end of the portion 14b. An indicating member 15 is removably mounted on the mounting portion 14c of the arm 14.

The indicating member 15 has a generally ring-like configuration as seen in FIGS. 3(a) to 3(c). The indicating member 15 has a first indicating portion or element 15a providing a lower half of a circle, the other upper half of which is shown by a broken line in FIG. 3(b). The indicating member 15 further has a second indicating portion or element 15b providing an upper half of another circle, the other lower half of which is shown by a broken line in FIG. 3(b). A pair of parallel connecting portions or elements 15c connect the opposite ends of the first and second indicating portions 15a and 15b to each other to complete the indicating member 15. A pair of mounting members 16 are securely mounted at or near connecting portions of the indicating member 15 between the first indicating portion 15a and the connecting portions 15c and each has a rectangular through-hole 17 formed therein. The indicating member 15 is mounted on the arm 14 with the mounting portion 14c of the latter fitted in the through-hole 17 of one of the mounting members 16 thereon. Each of the mounting members 16 has a pair of opposite mounting faces 16a and 16b or 16c and 16d. It is to be noted that the mounting face 16b is opposite the mounting face 16a though not shown in any of FIGS. 2 to 4 but shown in FIG. 5(a).

The first and second indicating portions 15a and 15b of the indicating member 15 are connected in an inclined relationship to each other by a predetermined angle denoted at α in FIG. 3(c). In particular, the plane defined by the second indicating portion 15b is inclined by an angle α with respect to the plane defined by the first indicating portion 15a (that is, the plane of FIG. 3(b). It is to be noted that the angle α, which will be hereinafter described, is shown in a rather exaggerated manner in FIG. 3(c). Further, the axes of the through-holes 17 in the mounting members 16 extend perpendicularly to the plane defined by the first indicating portion 15a of the indicating member 15.

A method of taking an X-ray photograph using the dental X-ray irradiation indicating device 10 of the present invention will be described subsequently with reference to FIGS. 5(a) and 5(b).

When an X-ray photograph is to be taken, at first a film package 6 is mounted on the adhering portion 12 of the supporting member 11 as shown in phantom in FIG. 2 by means of a bonding agent applied to the adhering portion 12. Then, one of the mounting members 16 is selected depending upon at which location a tooth for an object of photographing is in a pair of rows of teeth, and the mounting portion 14c of the arm 14 is fitted into the through-hole 17 of the selected mounting member 16 to mount the indicating member 15 on the supporting member 11. In the case shown in FIGS. 5(a) and 5(b), the indicating member 15 is mounted such that the mounting face 16b of the upper mounting member 16 in FIG. 5(a) is fitted with the mounting portion 14c of the arm 14 with the second indicating portion 15b thereof positioned on the upper side. Where the indicating member 15 is mounted in this manner, the second indicating portion 15b thereof opposes the film package 6 and has a certain inclination with respect to the film package 6. It is to be noted that the reason of such selection of the mounting face of the mounting member 16 will become apparent from the following description. In this condition, the film package 6 is inserted into an oral cavity of a patient together with the supporting member 11. Here, in case the tooth for an object of photographing is a tooth 1a, the film package 6 is positioned inside the tooth 1a (on the side adjacent the tongue) such that a substantially central portion thereof may coincide with the tooth 1a as seen in FIGS. 5(a) and 5(b). Subsequently, the bitten portions 13a and 13b of the supporting member 11 are bitten by the teeth 1a and 1b, respectively, so that the film package 6 may be held at the location. In this instance, due to presence of the gums 2, the film package 6 is held with a certain inclination with respect to a line interconnecting the teeth 1a and 1b, that is, to a vertical line D shown in a long and short dash line in FIG. 5(b) (perpendicular line to the bitten portions 13a and 13b). The inclination is substantially fixed for each of a tooth for an object of photographing. It is to be noted that, though not specifically shown, the bitten portions 13a and 13b of the supporting member 11 are actually distorted a little because the supporting member 11 is made of a comparatively soft material.

In the condition in which the film package 6 is held in such a manner as described above, the portion 14a of the arm 14 extends forwardly outwardly of the oral cavity and then laterally sidewardly farther than the thickness of the cheek 4. The second indicating portion 15b of the indicating member 15 is thus positioned in an opposing relationship to a substantially central portion of the film package 6 with a predetermined inclination α (about one half to the inclination of the film package 6). The arm 14 has such a configuration as to attain such positioning of the second indicating portion 15b of the indicating member 15. Subsequently, an X-ray irradiating device not shown is positioned such that an irradiating end face thereof may coincide with the plane defined by the second indicating portion 15b of the indicating member 15, and then an X-ray is emitted from the X-ray irradiating device. Thereupon, the X-ray is irradiated perpendicularly to the plane of the second indicating member 15b as indicated by a long and short dash line X in FIG. 5(b). Accordingly, an X-ray image (latent image) of the tooth 1a is produced with the substantially same size as the exact size on the X-ray film 7. The reason will be hereinafter described. After completion of X-ray irradiation, the film package 6 is taken out of the oral cavity together with the dental X-ray irradiation indicating device 10, and then the indicating member 15 is removed from the arm 14. Then, either after removal of or without removing the film package 6 from the supporting member 11, the X-ray film 7 is taken out of the film package 6, and predetermined developing and fixing operations are made for the X-ray film 7.

Here, the inclination of the second indicating portion 15b of the indicating member 15 and the reason why an X-ray image of the tooth 1a is obtained with the exact size will be described with reference to diagrammatic representations of FIGS. 6(a) and 6(b). It is assumed here that the film package 6 is held with an inclination of an angle $\theta$ with respect to the vertical line D and the tooth 1a has a length L (length between points $P_2$ and $P_3$) in the direction of the vertical line D. If an X-ray is thus irradiated in a direction perpendicular to the vertical line D, then the points $P_2$ and $P_3$ are projected at points $P_2'$ and $P_3'$, respectively, on the X-ray film as shown in FIG. 6(a). The distance between the points $P_2'$ and $P_3'$ is given by $L/\cos\theta$, and the dimension $L/\cos\theta$ is greater than the dimension L because $\cos\theta$ is smaller than 1. To the contrary, if an X-ray is irradiated in a direction perpendicular to the plane of the X-ray film, the points $P_2$ and $P_3$ are projected at points $P_2''$ and $P_3''$, respectively, on the X-ray film. The distance between the points $P_2''$ and $P_3''$ is given by $L\cdot\cos\theta$, and the dimension $L\cdot\cos\theta$ is smaller than the dimension L because $\cos\theta$ is smaller than 1. In this manner, where the film package 6 is held in an inclined position, if an X-ray is irradiated in a direction perpendicular to the vertical line D or to the plane of the X-ray film, an X-ray image of the exact size of a tooth cannot be obtained.

Here, means will be examined for obtaining an X-ray image of the exact size of a tooth. To this end, a line E is considered which has an inclination angle equal to one half of the inclination angle $\theta$ of the film package 6 as shown in FIG. 6(b). An X-ray is thus irradiated in a direction perpendicular to the line E. Consequently, the points $P_2$ and $P_3$ are projected at points $P_2'''$ and $P_3'''$ on the X-ray film. In this condition, the triangle $P_1$, $P_3$, $P_3'''$ defined by a point of intersection between the vertical line D and an extension line of the film package 6 and the points $P_3$ and $P_3'''$ is an isosceles triangle. Accordingly, the dimension between the points $P_2'''$ and $P_3'''$ is equal to the dimension L between the points $P_2$ and $P_3$. After all, where the film package 6 is held in an inclined position, if an X-ray is irradiated in a direction perpendicular to a line or plane having an inclination angle equal to one half of the inclination angle of the film package 6, then an X-ray image of a tooth can be obtained with the exact size. The one half inclination angle corresponds to the angle $\alpha$ shown in FIG. 3(c).

The film package 6 is described held in an inclined position in the foregoing description. Actually, however, the dimensions of various portions of an oral cavity and configurations of rows of teeth and gums are different to some degree among individuals so that the film package 6 may not be inclined but remain in a vertical position. In this instance, if the mounting member 16 is selectively mounted at the mounting portion 14c of the arm 14 such that the first indicating portion 15a may oppose the film package 6, then the plane thereof is parallel to the plane of the film package 6. Accordingly, if X-ray photographing is conducted with the irradiating end face of the X-ray irradiating device held in the plane of the first indicating portion 15a of the indicating member 15, then an X-ray image of a tooth is obtained with the exact size on the X-ray film 7.

Generally, the inclination of the film package 6 substantially depends upon a location of a tooth for an object of photographing in a pair of rows of teeth. Description is given here of mounting of the film package 6 at the mounting portion 14c of the arm 14 when X-ray photographing of teeth at various locations in the rows of the teeth is to be effected. Selections of the mounting faces 16a to 16d of the mounting members 16 and the first and second indicating portions 15a and 15b are given below.

i. Left upper jaw . . . select mounting face 16b with indicating portion 15b positioned upwardly (inclined); select mounting face 16d with indicating portion 15a positioned upwardly (not inclined).
  ii. Left lower jaw . . . select mounting face 16d with indicating portion 15b positioned downwardly (inclined); select mounting face 16b with indicating portion 15a positioned downwardly (not inclined).
  iii. Right upper jaw . . . select mounting face 16d with indicating portion 15b positioned upwardly (inclined); select mounting face 16b with indicating portion 15a positioned upwardly (not inclined).
  iv. Left lower jaw . . . select mounting face 16b with indicating portion 15b positioned downwardly (inclined); select mounting face 16d with indicating portion 15a positioned downwardly (not inclined).
  v. Front upper jaw . . . select mounting face 16b or 16d with indicating portion 15b positioned upwardly (inclined); select mounting face 16b or 16d with indicating portion 15a positioned upwardly (not inclined).
  vi. Front lower jaw . . . select mounting face 16b or 16d with indicating portion 15b positioned downwardly (inclined); select mounting face 16b or 16d with indicating portion 15a positioned downwardly (not inclined).

In this manner, X-ray photographing of all teeth is covered by combinations of the first and second indicating portions 15a and 15b and the four mounting faces 16a to 16d of the mounting members 16.

As can be seen from the foregoing description, according to the present embodiment, the indicating member is mounted at the end of the arm extending from the supporting member in an opposing relationship to a film package by way of a selected one of combinations of the first and second indicating portions and the four mounting faces of the two mounting members. In this instance, when the film package is in a vertical plane, the indicating member is disposed in parallel to the vertical plane of the film package, but when the film package is in an inclined plane, the indicating member is disposed with an inclination equal to one half of the inclination of the plane of the film package. Accordingly, irradiation of an X-ray can be made readily and accurately and an X-ray image of a tooth can be obtained with the exact size, which will assure an accurate diagnosis and treatment.

Referring now to FIGS. 7(a) and 7(b), there are shown an indicating member and a mounting structure for the same of a dental X-ray irradiation indicating device according to a second embodiment of the present invention. It is to be noted that like parts or elements are denoted by like reference symbols to those of the first embodiment shown in FIGS. 2 to 4, and overlapping description thereof is omitted herein to avoid redundancy (this also applies to the following description of various embodiments and modifications of the present invention).

The indicating member denoted at 15 of the dental X-ray irradiation indicating device shown has a pair of projections 20 mounted thereon at or near connecting portions between a first indicating portion 15a and a pair of connecting members 15c thereof. A guide plate 21 in the form of a flat plate is secured to an end of each of the projections 20 and extends with substantially equal spans in the opposite directions from the end of the projection 20. Meanwhile, each of a pair of mounting members 16 has a pair of L-shaped holding pieces 22 formed at a pair of upper and lower ends of a side face thereof, and a slot 23 is thus defined by the side face and the holding pieces 22 of the mounting member 16. The mounting plate 16 can thus be mounted readily on the indicating member 15 by fitting one of the guide plates 21 into the slot 23 thereof and can be adjusted relative to the indicating member 15 by slidably moving the side guide plate 21 in the slot 23 thereof.

The conditions of the gums, rows of teeth, lips, cheeks and so on are different to some degree among individuals as described hereinabove. Due to such differences, the position of the mounting portion 14c of the arm 14 (refer to FIGS. 2 to 4) when the supporting member 11 is held in a bitten condition in an oral cavity in order to effect X-ray photographing is different more or less among individuals. Further, even with a same person, the position of the mounting portion 14c of the arm 14 may be different more or less depending upon a tooth for an object of photographing. There is the possibility, therefore, that, when a mounting member 16 is mounted on the mounting portion 14c of the arm 14, the indicating member 15 may be contacted with and distorted by an outer face of a cheek. Such distortion will cause failure in accurate photographing. According to the present embodiment, however, since the mounting member 16 can be slidably moved back and forth on the guide plate 21 relative to the indicating member 15, where there is the possibility that the indicating member 15 may be contacted with a cheek, the indicating member 15 can be positioned in a spaced relationship from the cheek by slidably displacing the mounting member 16 toward the cheek and mounting the thus adjusted mounting member 16 at the mounting portion 14c of the arm 14. The distance between the indicating member 15 and the cheek can also be adjusted suitably by such sliding displacement of the mounting member 16 on the guide plate 21.

It is to be noted that, while in the present embodiment the guide plates 21 are mounted on the indicating member 15 side and the slots for receiving the guide plates 21 therein are formed in the mounting bodies 16, the mounting members 16 may be secured reversely to ends of guide plates while guide slots or guide holes for receiving the guide plates therein are formed in the indicating member 15.

In this manner, according to the present embodiment, since the mounting members can be displaced in the forward and backward directions with respect to the indicating member, not only similar effects to those of the preceding first embodiment can be anticipated, but also the indicating member can be held in a suitably spaced relationship from an outer face of a cheek.

Referring now to FIGS. 8(a) to 8(d), there are shown an indicating member and a mounting structure for the same of a dental X-ray irradiation indicating device according to a third embodiment of the present invention. The indicating member 15 of the dental X-ray irradiation indicating device shown has a pair of mounting plates 25 mounted thereon at or near connecting portions between a first indicating portion 15a and a pair of connecting portions 15c thereof. A pin 26 is implanted on each of the mounting plates 25, and a pivotal member 26 is mounted for pivotal motion on the pin 26. The pivotal member 27 has a mounting member 16 secured to an end thereof. In FIG. 8(a), the left-hand side pivotal member 27 is shown in its horizontal position while the right-hand pivotal member 27 is shown in its upwardly pivoted position.

Each of the mounting plates 25 has, as particularly seen in FIGS. 8(c) and 8(d), up to four grooves 29a, 29b, 29c and 29d formed in vertical and horizontal directions in an angularly spaced relationship by 90 degrees in a wall thereof. The pin 26 is provided at a crossing location of the grooves 29a to 29d on the mounting plate 25 and has an enlarged head portion 26a formed at an end thereof and a diametrical slit 26b formed therein. Meanwhile, each of the pivotal plates 27 has a projection 28 provided at a location thereon near a hole in which the pin 26 is fitted.

In order to fit a pivotal member 27 onto a pin 26, the pivotal member 27 is pressed at the hole thereof strongly against the pin 26. Consequently, the pin 26 is distorted to reduce the slit 26b thereof so that the diameter of the enlarged head portion 26a is reduced to allow the pin 26 to be fitted into the hole of the pivotal member 27. After the pivotal member 27 is fitted onto the pin 26, the pin 26 is restored to its original shape expanding the slit 26b to expand the enlarged head portion 26a. Consequently, the pivotal member 27 is thereafter prevented from coming off from the pin 26. If the pivotal member 27 is pivoted in this condition, the projection 28 thereon will slidably move on a surface of the mounting plate 25 until it is fitted into one of the grooves 29a to 29d in the mounting plate 25, but if the pivotal member 27 is pivoted further, the projection 28 thereon will be removed from the one groove and then fitted into an adjacent next one of the grooves 29a to 29d. With the projection 28 thus fitted in one of the grooves 29a to 29d, the pivotal member 27 is retained at the position.

The dental X-ray irradiation indicating device of the present embodiment can prevent possible contact of the indicating member 15 with a cheek similarly as in the preceding embodiment. In particular, when X-ray photographing is to be effected, one of the pivotal members 27 to which the mounting member 16 to be mounted at the mounting portion 14c of the arm 14 is secured is pivoted until the projection 28 thereon is fitted into the groove 29a or 29d of the mounting plate 25 to retain the pivotal member 27 at its horizontal position. The mounting member 16 is then mounted onto the mounting portion 14c of the arm 14. As a result, the indicating member 15 can be held at a position spaced from an outer face of a cheek.

In this manner, according to the present embodiment, since the pivotal members are mounted for pivotal motion on the indicating member and the mounting members are secured to ends of the pivotal members, not only similar effects to those of the second embodiment can be attained, but also the pivotal members and the mounting members can be prevented from interfering with some other elements upon photographing or upon storage of the indicating member if an unnecessary one of the pivotal members is retained at the upwardly pivoted position.

Referring to FIGS. 9(a) to 9(d), there are shown an indicating member and a mounting structure for the same of a dental X-ray irradiation indicating device according to a fourth embodiment of the present invention. The indicating member denoted at 15' of the dental X-ray irradiation indicating device shown corresponds to the indicating member 15 of the first to third embodiments described hereinabove. The indicating member 15' of the present embodiment is different from the indicating member 15 of the preceding embodiments in that a first indicating portion 15a and a pair of connecting members 15c thereof are coupled to each other by a pair of pivotally connecting means 31 and 32.

The pivotally connecting means 31 includes, as shown in FIG. 9(b), a plate-formed member 31c secured to or molded in an integral relationship with one of the connecting members 15c, another plate-formed member 31a secured to or molded in an integral relationship with one end of the first indicating portion 15a, and a pin 31p for connecting the plate-formed members 31c and 31a for pivotal motion relative to to each other. Meanwhile, the other pivotally connecting means 32 includes, as shown in FIG. 9(c), a plate-formed member 32c secured to or molded in an integral relationship on the other connecting member 15c, another plate-formed member 32a secured to or molded in an integral relationship on the other end of the first indicating portion 15a, and a screw 32b for securing the plate-formed members 32c and 32a to each other. A nut 32n is secured to the end of the screw 32b. The plate-formed member 32c has a mark 33a applied at an end portion thereof while several graduations 33b are applied to the other plate-formed member 32a of the pivotally connecting means 32 in an opposing relationship to the mark 33a as shown in FIG. 9(d).

Since the conditions of the oral cavity are different to some degree among individuals as described hereinabove, when the supporting member 11 is bitten and held in the oral cavity and the indicating member 15 is mounted on one of the mounting members 16 at the mounting portion 14c of the arm 14 thereof, the plane defined by the first and second indicating portions 15a and 15b may not always be inclined by an angle equal to one half of such an inclination angle θ of the film package 6 as shown in FIG. 6(b). In such an instance, there is the possibility that a desired degree of accuracy may not always be attained in X-ray photographing. In the present embodiment, however, the inclination of the indicating member 15 can be adjusted readily in such an instance. In particular, if the screw 32b of the pivotally connecting portion 32 is loosened, then a pivotal motion of the plate-formed members 32c and 32a relative to each other (a pivotal motion between the first indicating member 15a and the connecting member 15c) is permitted. Meanwhile, the pivotally connecting means 31 always permits a pivotal motion between the plate-formed members 31c and 31a. Accordingly, the angle between the first and second indicating portions 15a and 15b can now be changed freely. A change of the angle can be discriminated from the mark 33a and the graduations 33b of the pivotally connecting means 32. After a desired plane is obtained by such pivotal motion between the first and second indicating portions 15a and 15b, the screw 32b is tightened to fix the plate-formed members 32c and 32a relative to each other, and in this condition, X-ray photographing is conducted.

In this manner, according to the present embodiment, since the pivotal means are interposed between the first indicating portion and the connecting portions, an effect can be exhibited, in addition to the effects of the first embodiment described hereinabove, that the inclination of the plane of the indicating member can be adjusted.

In the preceding four embodiments of the present invention, the indicating member 15 is composed of a pair of semicircular portions and a pair of connecting portions for interconnecting the semicircular portions. To the contrary, in the following embodiments described below, the indicating member is composed of a member of a single circle.

Referring first to FIGS. 10 to 13, there is shown a dental X-ray irradiation indicating device according to a fifth embodiment of the present invention. The dental X-ray irradiation indicating device shown is generally denoted at 40 and includes a supporting member 41 in the form of a parallelepiped having a rectangular cross section and made of a soft material such as, for example, sponge, foamed polyethylene, or rubber. The supporting member 41 has an adhering portion or face 42 for adhering a film package 6 thereto. The supporting member 41 further has a pair of upper and lower bitten faces or portions 43a and 43b adapted to be bitten by upper and lower opposing teeth when an X-ray photograph is to be taken.

An arm 44 having a substantially U-shape in plan extends from the supporting member 41. The arm 44 has a portion 44a extending laterally from an end of the supporting member 41 and having a face in the common plane with a face of the supporting member 41 opposite the adhering face or portion 42, another portion 44b contiguous to the portion 44a and extending in a direction substantially perpendicular to the portion 44a, a further portion $44c_1$ contiguous to the portion 44b and extending in a direction substantially perpendicular to the portion 44b, and an end portion $44c_2$ of the portion $44c_1$. An indicating member 45 is removably mounted on the end portion $44c_2$ of the arm 44. The indicating member 45 has a generally ring-like configuration as seen in FIGS. 10, 11 and 13, and the indicating member 45 will be hereinafter referred to as a ring. The ring 45 has a plurality of mounting members 46a, 46b, 46c and 46d for mounting the ring 45 on the arm 44. Each of the mounting members 46a to 46d is mounted on the ring 45 by means of a support member 47a, 47b (not shown), 47c or 47d and has a hole 48 formed therein. The ring 45 is thus mounted on the arm 44 of the supporting member 41 as shown in FIG. 13 with the end portion $44c_2$ of the arm 44 fitted in the hole 48 of one of the mounting members 46a to 46d of the ring 45. The shape and size of the arm 44 and the size of the ring 45 are selected such that, when the ring 45 is mounted on the arm 44, a central portion of the ring 45 may be positioned in a substantially opposing relationship to the center of a film package 6 mounted in position on the mounting member 41.

The angles at which the arm 44 is mounted on the mounting members 46a to 46d of the ring 45 are different from each other including orientations thereof. As for the mounting member 46b, for example, a vertical line A parallel to a pair of opposing ones of of four inner wall faces of the hole 48 thereof is inclined by an angle $\alpha_2$ with respect to the plane of the ring 45 as shown in FIG. 12(a). Meanwhile, a vertical line A of the mounting member 46c is inclined by an angle $\alpha_3$ with respect to the plane of the ring 45 as shown in FIG. 12(b). Here, the angles $\alpha_2$ and $\alpha_3$ are different in value from each other. The mounting members 46a and 46d similarly have inclinations with respect to the ring 45 and are also different in orientations thereof from those of the mounting members 46b and 46c. In order to facilitate understandings, the inclinations are shown in a rather exaggerated manner in FIGS. 11, 12(a) and 12(b). It is to be noted that all of the components of the dental X-ray irradiation indicating device 40 are made of materials which transmit an X-ray therethrough.

A method of taking an X-ray photograph using the dental X-ray irradiation indicating device 40 of the present embodiment will be described subsequently with reference to FIGS. 14(a) and 14(b).

When an X-ray photograph is to be taken, at first a film package 6 is mounted on the adhering portion 42 of the supporting member 41 as shown in phantom in FIG. 10 by means of a bonding agent applied to the adhering portion 42. Then, one of the mounting members 46a to 46d, for example, the mounting member 46b, is selected depending upon at which location a tooth for an object of photographing is in a row of teeth, and the end portion $44c_2$ of the arm 44 of the supporting member 41 is fitted into the hole 48 of the selected mounting member 46b to mount the ring 45 on the supporting member 41. Where the ring 45 is mounted in this manner, it has a certain inclination with respect to the film package 6. In this condition, the film package 6 is then inserted into an oral cavity of a patient together with the supporting member 41 of the dental X-ray irradiation indicating device 40. Here, in case the tooth for an object for photographing is a tooth 1a, the film package 6 is positioned inside the tooth 1a (on the side adjacent the tongue 3) such that a substantially central portion thereof may coincide with the tooth 1a as shown in FIGS. 14(a) and 14(b). Subsequently, the bitten portions 43a and 43b of the supporting member 41 are bitten by the teeth 1a and 1b, respectively, so that the film package 6 may be held at the location. In this instance, due to presence of the gums 2, the film package 6 is held with a certain inclination with respect to a line interconnecting the teeth 1a and 1b, that is, to a vertical line D shown in a long and short dash line in FIG. 14(b) (perpendicular line to the bitten portions 43a and 43b). Since the inclination is substantially fixed for each of a molar of the upper jaw, a molar of the lower jaw, a front tooth of the upper jaw and a front tooth of the lower jaw as described hereinabove, one of the mounting members 46a to 46d is selected depending upon which one of the teeth is the tooth 1a for an object of photographing. The ring 45 is thus mounted on the supporting member 41 with an inclination equal to one half of the inclination of the film package 6 with respect to the vertical line D by fitting a selected one of the mounting members 46a to 46d thereof onto the arm 44. In this instance, since the inclination of the film package 6 is substantially fixed for each of a molar of the upper jaw, a molar of the lower jaw, a front tooth of the upper jaw and a front tooth of the lower jaw as described above, where the four mounting members 46a to 46d are mounted on the ring 45 so as to conform to the different teeth, the single ring 45 can be used for any of left-hand side teeth in upper and lower tooth rows without little trouble. It may be seen from this fact that X-ray photographing of all teeth can be covered if a complementary ring is prepared wherein the mounting members 46a to 46d are arranged in a symmetrical relationship to those of the ring 45 shown in FIGS. 10 to 13.

In this manner, according to the present embodiment, since one of the four mounting members different in angle and mounted around the ring is selectively mounted at the end of the arm extending from the supporting member such that the ring may oppose to a film package supported in position on the supporting member and have an inclination equal to one half of the inclination of the film package, similar effects to those of the first embodiment described hereinabove can be attained.

Referring now to FIGS. 15(a) and 15(b), there is shown part of a dental X-ray irradiation indicating device according to a sixth embodiment of the present invention. The dental X-ray irradiation indicating device shown includes a ring 45 similar to the ring 45 in the fifth embodiment shown in FIGS. 10 to 13. The ring 45 has a pair of mounting blocks 50a and 50b mounted at symmetrical locations thereon and having such an arcuate configuration as seen in FIG. 15(b). The mounting block 50b has four rectangular holes $51b_1$, $51b_2$, $51b_3$ and $51b_4$ formed in a row therein. The hole $51b_1$ has an inclination of a predetermined angle $\theta$ with respect to a line perpendicular to the plane of the ring 45. The other holes $51b_2$ to $51b_4$ also have individually different inclinations with respect to the perpendicular line. Though not specifically shown, also the mounting block 50a has four similar holes formed therein with individually different inclinations.

Upon X-ray photographing, if the end portion $44c_2$ of the arm 44 shown in FIG. 10 is inserted into a selected one of the holes of a selected one of the mounting blocks 50a and 50b, then the ring 45 can be held in a predetermined inclination with respect to the film package 6 supported in position. For example, where the hole $51b_1$ is selected, an inclination of the ring 45 most suitable for X-ray photographing of a molar of the left lower jaw is obtained. If the hole $51b_2$, $51b_3$ or $51b_4$ is selected, then an inclination of the ring 45 most suitable for X-ray photographing of a front tooth of the left lower jaw, a front tooth of the left upper jaw or a molar of the left upper jaw, respectively, is obtained.

It is to be noted that while in the sixth embodiment the ring is described having two mounting blocks mounted in a symmetrical relationship thereon, apparently it may otherwise have thereon only one mounting block in which a required number of holes having individually predetermined inclinations are formed. It is also apparent that the mounting block or blocks need not be formed in an arcuate configuration. Further, while the mounting blocks are shown mounted at substantially central portions thereof on the ring, each of them may be mounted at any other portion thereof on the ring.

In this manner, according to the present embodiment, since the plurality of holes adapted to receive therein the end of the arm of the supporting member are formed individually with predetermined angles in the mounting block secured to the ring, not only similar effects to those of the fifth embodiment described above are exhibited, but also the dental X-ray irradiation indicating device is simple in structure and easy in production.

Referring now to FIGS. 16(a) to 16(c), there is shown a dental X-ray irradiation indicating device according to a seventh embodiment of the present invention. The dental X-ray irradiation indicating device shown includes a supporting member 41 having thereon a modified arm 44' which is different from the arm 44 of the fifth and sixth embodiments described hereinabove. In particular, while the arm 44 of the fifth and sixth embodiments has the portion 44b and the contiguous portion $44c_1$, the arm 44' of the present embodiment does not have a portion corresponding to the portion $44c_1$. Accordingly, an end portion $44c_2$ is present on the portion 44b. With the construction of the arm 44', a ring 45 is mounted in a different orientation by an angle of 90 degrees from that in the fifth and sixth embodiments. The ring 45 shown in FIGS. 16(b) and 16(c) is designed to conform to such mounting. Referring to FIGS. 16(b) and 16(c), the ring 45 shown has a pair of mounting blocks 53a and 53b mounted in a symmetrical relationship thereon. The mounting blocks 53a and 53b have rectangular holes $54a_1$, $54a_2$, $54a_3$ and $54a_4$ and $54b_1$, $54b_2$, $54b_3$ and $54b_4$ formed therein, respectively, and are secured to the ring 45 each by means of a fixing pin 55a or 55b, respectively.

The mounting blocks 53a and 53b of the present embodiment are different from the mounting blocks 50a and 50b of the sixth embodiment in that while open ends of the holes $51a_1$ to $51a_4$ and $51b_1$ to $51b_4$ formed in the mounting blocks 50a and 50b, respectively, of the sixth embodiment extend in a direction perpendicular to the plane of the ring 45, open ends of the holes $54a_1$ to $54a_4$ and $54b_1$ and $54b_4$ formed in the mounting blocks 53a and 53b, respectively, of the present embodiment extend in a plane substantially in the same direction as the plane of the ring 45. The holes $54a_1$ to $54a_4$ and $54b_1$ to $54b_4$ have individually different inclinations as seen in FIG. 16(c).

Upon X-ray photographing, if the end portion $44c_2$ of the arm 44 shown in FIG. 16(a) is inserted into a selected one of the holes $54a_1$ to $54a_4$ and $54b_1$ to $54b_4$, then the ring 45 can be positioned with a predetermined inclination with respect to the film package 6 supported in position in an opposing relationship to the film package 6 similarly as in the sixth embodiment described hereinabove. Selection of one of the holes is made depending upon a tooth for an object of photographing as described hereinabove in connection with the fifth and sixth embodiments.

It is to be noted that the ring may otherwise have thereon only one mounting block and that a required number of holes may be formed in the mounting block. Further, the locations of the mounting blocks on the ring are not limited to the specific ones shown in FIG. 16(b) but may be displaced upwardly or downwardly in FIG. 16(b). In addition, each of the mounting blocks may be mounted directly on the ring without using a fixing pin.

In this manner, according to the present embodiment, since the plurality of holes adapted to receive therein the end of the arm of the supporting member are formed individually with predetermined angles in the mounting block secured to the ring, similar effects to those of the sixth embodiment described above are attained.

Referring now to FIGS. 17(a) to 17(c), part of a dental X-ray irradiation indicating device according to an eighth embodiment of the present invention is shown. The dental X-ray irradiation indicating device shown includes a ring 45 having a single mounting block 56 securely mounted thereon by means of a pin 60. An angular position defining key 61 is formed in a contiguous relationship to the pin 60 on the ring 45. The mounting block 56 mounted on the ring 45 has a hole 57 formed therein and up to four pin holes 58a, 58b, 58c and 58d perforated therein in a perpendicular relationship to the hole 57. The mounting block 56 further has slits 59a, 59b, 59c and 59d formed therein in a contiguous relationship to the pin holes 58a to 58d, respectively.

In the dental X-ray irradiation indicating device of the present embodiment, the supporting member 41 having the arm 44' shown in FIG. 16(a) is used as a supporting member. The hole 57 of the mounting block 56 is thus adapted to receive the end portion $44c_2$ of the arm 44' of the supporting member 41. The mounting block 56 is formed as a separate member from the ring 45 and removably mounted on the ring 45 by inserting the pin 60 of the ring 45 into one of the pin holes 58a to 58d of the mounting block 56. When the pin 60 is inserted into one of the pin holes 58a to 58d, the angular position defining key 61 contiguous to the pin 60 is fitted into one of slits 59a to 59d contiguous to the one pin hole 58a, 58b, 58c or 58d, respectively.

When X-ray photographing is to be conducted, the pin 60 of the ring 45 is inserted into a selected one of the pin holes 58a to 58d of the mounting block 56 to connect the ring 45 to the mounting block 56, and then the end portion $44c_2$ of the arm 44 of the supporting member 41 is inserted into the hole 57 of the mounting block 56. The ring 45 is thus mounted on the arm 44' of the supporting member 41 in an inclined position by a predetermined angle which is determined by the angular position defining key 61 and one of the slits 59a to 59d in which the key 61 is fitted. For example, if the pin 60 is inserted into the pin hole 58a of the mounting block 56 with the angular position defining key 61 fitted into the slit 59a contiguous to the pin hole 58a, the angular position of the plane of the ring 45 with respect to the mounting direction of the hole 57 is defined by the inclination of the slit 59a. If the end portion $44c_2$ of the arm 44' of the supporting block 41 is fitted into the hole 57 of the mounting block 56, then the plane of the ring 45 presents an inclination most suitable for photographing of a molar of the left lower jaw. When any other pin hole is selected in a similar manner, the plane of the ring 25 is disposed in an inclination most suitable for photographing of a corresponding tooth.

It is to be noted that while in the eighth embodiment the ring is described including a single mounting block, it may otherwise include a pair of mounting blocks similarly to the sixth and seventh embodiments described above. Further, while the slits are described formed in one wall face of the mounting block, they may be additionally formed in the opposing wall face of the mounting block, and with such a modified mounting block, inclinations suitable for photographing of all of the teeth can be provided by the single block. Meanwhile, if the pin is secured perpendicularly to the plane of the ring, then the supporting member having such an arm as shown in FIG. 10 can be used for the ring.

In this manner, according to the present embodiment, since the mounting block has formed therein the single hole for engaging with the arm, the plurality of pin holes for engaging with the pin mounted on the ring and the plurality of slits for engaging with the angular position defining key, similar effects to those of the sixth embodiment can be anticipated.

Referring now to FIG. 18, there is shown a mounting block of a dental X-ray irradiation indicating device according to a ninth embodiment of the present invention. The mounting block denoted at 56' has a hole 57' and a single pin hole 58 formed therein. The mounting block 56' further has up to four slits 59a', 59b', 59c' and 59d' formed therein in a contiguous relationship to the pin hole 58 and extending radially from the pin hole 58. The mounting block 56' of the present embodiment may be used in place of the mounting block 56 of the eighth embodiment shown in FIG. 17(c). If the pin 60 of the ring 45 is inserted into the hole 58 with the contiguous angular position defining key 61 fitted into a selected one of the slits 59a' to 59d', the plane of the ring 45 can be set in an angular position suitable for photographing of a desired tooth.

Since the mounting block of the present embodiment has only one pin hole formed therein, the dental X-ray irradiation indicating device exhibits, in addition to the same effects with the eighth embodiment, an effect that it can be further simplified in structure.

FIGS. 19(a) and 19(b) show a dental X-ray irradiation indicating device according to a tenth embodiment of the present invention. The dental X-ray irradiation indicating device shown includes a ring 45 and a guide plate 63 secured to the ring 45 by welding. The guide plate 63 is formed into an arcuate configuration of a predetermined curvature as seen in FIG. 19(b) and is welded at a substantially central portion thereof to the ring 45. A movable member 64 is mounted for sliding movement on the guide plate 63. The movable member 64 has a through-hole 64a perforated therein and has a pair of engaging pieces 64b formed thereon for slidably engaging with the guide plate 63. Also in the dental X-ray irradiation indicating device of the present embodiment, the supporting member 41 having the arm 44' shown in FIG. 16(a) is used similarly to the eighth embodiment described hereinabove, and the end portion $44c_2$ of the arm 44' of the supporting member 41 is fitted in the hole 64a of the movable member 64.

When X-ray photographing is to be conducted, at first the movable member 64 is slidably moved on the guide plate 63. During such sliding movement of the movable member 64, the inclination of the hole 64a of the movable member 64 varies continuously. When a predetermined inclination of the hole 64a is reached, the movable member 64 is stopped, and then if the end portion $44c_2$ of the arm 44' of the supporting member 41 is inserted into the hole 64a, a predetermined inclination of the plane of the ring 45 is obtained. In order to facilitate discrimination of a desired inclination of the plane of the ring 45, various means may be provided. For example, graduations may be applied to the guide plate 63, or a positioning mechanism of the click stop type may be provided between the guide plate 63 and the movable member 64.

It is to be noted that while in the present embodiment the guide plate is described provided on only one side of the ring, it may be additionally provided also on the other side of the ring. Further, while the guide plate is secured at a substantially central portion thereof to the ring, it may otherwise be secured to the ring at some other portion thereof, for example, at an upper end portion thereof, in accordance with the curvature of the arc of the arcuate guide plate. Further, if the orientation of the guide plate is changed by an angle of 90 degrees, that is, if the guide plate is mounted on the ring such that a side wall thereof may be directed forwardly in FIG. 19(a), the supporting block having the arm shown in FIG. 10 can be applied to the ring of the present embodiment.

In this manner, according to the present embodiment, since the movable member having the hole formed therein is mounted for sliding movement on the guide plate, similar effects to those of the sixth embodiment described hereinabove can be anticipated, and besides the dental X-ray irradiation indicating device can be further simplified in structure.

In the first to tenth embodiments of the present invention described hereinabove, substantially a plurality of mounting members are mounted on a single indicating member. To the contrary, in an eleventh embodiment of the present invention which will be described in the following, a single mounting member is provided for a single indicating member.

Referring to FIGS. 20(a) and 20(b), a dental X-ray irradiation indicating device of the eleventh embodiment includes an indicating member 65 adapted to be mounted at an end portion $44c_2$ of an arm 44 of a supporting member 41. The indicating member 65 includes a mounting member 65a having a fitting hole 65b formed therein for fitting with the end portion $44c_2$ of the arm 44, a bar-like member 65c secured to the mounting member 65a, and an indicating element 65d secured to the bar-like member 65c. The indicating element 65d has a substantially circular configuration and has an inclination equal to one half of an estimated inclination of a film package 6 to be supported on the supporting member 41. It is to be noted that naturally the supporting member 41 including the arm 44 and the indicating member 65 are individually made of materials which transmit an X-ray therethrough. The inclination of the film package 6 is substantially fixed for each of a molar of the upper jaw, a molar of the lower jaw, a front tooth of the upper jaw and a front tooth of the lower jaw as described hereinabove, and the inclinations are not very different in magnitude from each other. Accordingly, even if the inclination of the indicating element 65d is set fixedly as in the present embodiment, there is no substantially trouble. Up to eight indicating members, however, may be provided for left and right molars of the upper jaw, left and right molars of the lower jaw, left and right front teeth of the upper jaw and left and right front teeth of the lower jaw so as to cope with all of the teeth.

It is to be noted that while in the present embodiment the hole which is opened only at an end thereof is shown as a fitting hole of the indicating member, if the hole is otherwise formed as a through-hole which is opened at the opposite ends thereof, then the number of required types of indicating members can be reduced by half. Further, the means for mounting the indicating member on the arm is not limited to the fitting hole and may be any other suitable means.

In this manner, according to the present embodiment, since the indicating member includes the indicating element secured to the mounting member and having an inclination equal to substantially one half of the inclination of a film package to be supported in position on the supporting member, similar effects, to those of the first embodiment described hereinabove can be anticipated with a simplified construction.

Referring now to FIGS. 21(a) and 21(b), there is shown a dental X-ray irradiation indicating device according to a twelfth embodiment of the present invention. While in any of the preceding embodiments an indicating member is formed as a separated member from a supporting member, in the present embodiment, an indicating member is formed as a unitary member together with a supporting member. In particular, the dental X-ray irradiation indicating device general denoted at 70 includes an indicating element 71 formed at an end of an end portion $44c_2'$ which extends obliquely upwardly from a portion $44c_1$ of an arm 44'' of a supporting member 41. The plane of the indicating element 71 has an inclination equal to one half of an estimated inclination of a film package 6 to be adhered to the supporting member 41.

In this manner, according to the present embodiment, since the supporting member including the arm and the indicating element are formed as a unitary member, similar effects to those of the eleventh embodiment can be attained with a further simplified construction.

Referring now to FIG. 22, a dental X-ray irradiation indicating device according to a thirteenth embodiment of the present invention is shown. The dental X-ray irradiation indicating device 70' of the present embodiment is similar in construction to the dental X-ray irradiation indicating device 70 of the preceding embodiment shwon in FIGS. 21(a) and 21(b) but is different in that it has an indicating element 72 in addition to an indicating element 71. In particular, a portion $44c_2$ extends obliquely upwardly from a portion $44c_1$ of an arm 44''' of a supporting member 41 while another portion $44c_3$ extends obliquely downwardly from the portion $44c_1$ of the arm 44''' in a contiguous relationship to the portion $44c_2$. The indicating element 72 is formed at an end of the portion $44c_3$ while the indicating element 71 is formed at an end of the portion $44c_2$. When a film package 6 is adhered to the supporting member 41 in such a manner that it extends downwardly below the supporting member 41 in a condition reverse to that shown in a long and short dash line in FIG. 21(a), the indicating element 72 is positioned in an opposing relationship to a substantially central portion of the film package and has an inclination equal to one half of the inclination of the film package 6.

With the dental X-ray irradiation indicating device 70' of the present embodiment having such a construction as described just above, apparently the indicating element 71 is used similarly to the eleventh embodiment described hereinabove when a photograph of a left tooth of the upper jaw or a right tooth of the lower jaw is to be taken, but when a photograph of a right tooth of the upper jaw or a left tooth of the lower jaw is to be taken, the indicating element 72 is used.

In this manner, according to the present embodiment, since the two indicating elements are provided, an effect can be anticipated, in addition to similar effects to those of the eleventh embodiment described hereinabove, that X-ray photographs of all of the teeth can be taken with the single dental X-ray irradiation indicating device.

In the first to thirteenth embodiments described hereinabove, an arm is shown formed as a unitary member together with a supporting member, and a film package is shown to be adhered to such a supporting member. It is naturally possible, however, to form an arm otherwise as a separate member from a supporting member. It is also possible to support a film package on a supporting member by some other means than adhesion. Thus, several examples of construction wherein an arm and a supporting member are formed as separate members from each other will be described below.

FIGS. 23(a) and 23(b) show a first example of coupling structure between a supporting member and an arm. The coupling structure shown includes a supporting member 121 and an arm 124. The supporting member 121 includes first and second members 122 and 123 made of a soft material such as foamed polyethylene and having a shape of a parallelepiped. The first member 122 has a bitten face or portion 122a while the second member 123 has a bitten face or portion 123a. The first and second members 122 and 123 have further faces 122c and 123c, respectively, having a bonding agent applied thereto.

The arm 124 is made of a synthetic resin material and has a portion 124a extending from the supporting member 121, another portion 124b contiguous to the portion 124a and extending in a direction perpendicular to the portion 124a, an indicating member mounting portion 124c at an end of the portion 124b, and a plate-formed portion 124c held between the first and second members 122 and 123 of the supporting member 121. The plate-formed portion 124c has a bonding agent applied to the opposite faces thereof, and the faces 122b and 123b of the first and second members 122 and 123, respectively, are secured to the opposite faces of the plate-formed portion 124d of the arm 124 by adhesion of the bonding agent. In this instance, the plate-formed portion 124d of the arm 124 and the first and second members 122 and 123 of the supporting member 121 are adhesively secured to each other such that at least the bonding agent applied faces 122c and 123c of members 122 and 123 may lie substantially in the same plane.

When an X-ray photograph is to the taken, a film package 6 is adhered to the supporting member 121 as seen in FIGS. 23(a) and 23(b) by the bonding agent applied to the bonding agent applied faces 122c and 123c of the first and second members 122 and 123, respectively, of the supporting member 121. A mounting portion of an indicating member not shown is then inserted into the indicating member mounting portion 124c of the arm 124 to mount the indicating member on the arm 124.

In this manner, according to the present coupling structure, since the pair of members each having the bitten portion thereon are adhered to the opposite faces of the plate-formed portion provided on the arm, a material for such supporting members in production may be little consumed uselessly and each of such supporting members can be cut off from the material by a simple cutting operation.

FIG. 24 shows a second example of coupling structure between a supporting member and an arm. The coupling structure shown has a generally similar construction to that of the coupling structure shown in FIGS. 23(a) and 23(b) and includes a supporting member 121' which is composed of a single member 122'. The member 122' has a bitten portion or face 122a' and an opposing adhered face 122b'. Meanwhile, a plate-formed portion 124d of an arm has a bonding agent applied to a face thereof and is adhered at the face thereof to the adhered face 122b' of the member 122' by the bonding agent. The opposing face of the plate-formed portion 124d of the arm 124 thus makes the other bitten portion or face of the supporting member 121'.

According to the present coupling structure, since the member of the supporting member is applied to only one face of the plate-formed portion of the arm, similar effects to those of the first coupling structure described hereinabove can be attained, and besides an additional effect can be anticipated that steps of applying a bonding agent to the plate-formed portion of the arm adhering the member to the plate-formed portion of the arm can be reduced by half.

Referring now to FIG. 25, there is shown a third example of coupling structure between a supporting member and an arm. The coupling structure shown has a generally similar construction to that of the coupling structure shown in FIG. 24 and includes an arm having a plate-formed portion 124d from which a supporting wall 124e extends in a perpendicular direction. In the case of the present coupling structure, a single member 122' of a supporting member 122' is not provided with a face to which a bonding agent is applied for adhering a film package 6 thereto. Instead, a suitable gap is provided between the supporting wall 124e of the arm 124 and an opposing face of the member 122', and in order to support a film package 6 on the supporting member 121, the film package 6 is put into the gap thus provided.

With the present coupling structure, since the supporting wall is formed in a continuous relatonship on the plate-formed portion of the arm, not only similar effects to those of the second coupling structure shown in FIG. 24 can be attained, but also a step of applying a bonding agent for adhering a film package can be eliminated and mounting and removal of a film package can be facilitated.

Referring now to FIGS. 26(a) and 26(b), there is shown a fourth example of coupling structure between a supporting member and an arm. The coupling structure includes a supporting member 121' composed of a single member 122' which has a pair of opposing upper and lower bitten portions or faces $122a_1'$ and $122a_2'$ thereon. The member 122' further has a pierced face 122d'. Meanwhile, an arm 124' has, in addition to such portions 124a and 124b as in the arm shown in FIG. 23(a), a forked piercing portion 124f thereon. The piercing portion 124f has a pair of halberd portions 124f₁ and 124f₂ and a plurality of claws 124g and 124h formed on the halberd portions 124f₁ and 124f₂.

Fixation of the arm 124' to the supporting member 121' is attained by piercing the piercing portion 124f of the arm 124' into the pierced face 122d' of the supporting member 121'. Since the supporting member 121' is made of a soft material, such piercing can be done readily. The piercing portion 124f of the arm 124' is pierced into the supporting member 121' until root portions of the halberd portions 124f₁ and 124f₂ are substantially contacted with the pierced face 122' of the supporting member 121'. Even if a force is applied to the arm 124' or the supporting member 121' in a direction to pull off the arm 124' and the supporting member 121' from each other when the piercing portion 124f is in a pierced condition in the supporting member 121' in this manner, the claws 124g and 124h will be pierced in the reverse directions into the supporting member 121'. Consequently, the arm 124' and the supporting member 121' are prevented from coming off from each other, thereby attaining certain fixation therebetween.

In this manner, with the present coupling structure, since the piercing portion of the arm is pierced into the supporting member to fix the two members to each other, not only similar effects to those of the first coupling structure shown in FIGS. 23(a) and 23(b) can be attained, but also a step of applying a bonding agent and an adhering step for fixation can be eleminated while the two members can be fixed to each other by a single operation of piercing, which facilitates production of the coupling structure.

FIG. 27 shows part of a fifth example of coupling structure between a supporting member and an arm. It is to be considered that other portions of the coupling structure which are not specifically shown in FIG. 27 are similar to those of the fourth coupling structure shown in FIGS. 26(a) and 26(b). In particular, the coupling structure shown in FIG. 27 is different from the fourth coupling structure in that a double-sided hook 124i is provided at an end of each of a pair of halberd portions 124f₁' and 124f₂' of a forked piercing portion 124f' of an arm 124'. The hooks 124i here serve also as acute piercing ends of the halberd portions 124f₁' and 124f₂'. With the construction, the coupling structure is simplified in construction of the piercing portion thereof comparing with the fourth coupling structure shown in FIGS. 26(a) and 26(b).

Referring now to FIG. 28, there is shown a sixth example of coupling structure between a supporting member and an arm. The coupling structure shown includes an arm 124'' having a holding portion 124j thereon. The holding portion 124j of the arm 124'' has a channel-like shape in plan and is connected at one of a pair of opposing sides thereof to a portion 124a of the arm 124''. The dimension between a pair of inner faces of the opposing sides of the holding portion 124j is selected to be substantially equal to the dimension between a pair of corresponding opposing faces of a single member 122' of a supporting member 121'. An inclined face 124j' is provided at an end of each of the sides of the holding portion 124j, and a plurality of claws 124k are provided on the inner faces of the opposite sides of the holding portion 124j while a plurality of claws 124l are provided on an inner face of a connecting side of the holding portion 124j.

Fixation of the arm 124'' to the supporting member 121' is attained by fitting the member 122' of the supporting member 121' into the holding portion 124j of the arm 124''. Here, even if the inner dimension of the holding portion 121j is a little smaller than the outer dimension of the member 122', fitting of the member 122' into the holding portion 124j of the arm 124'' can be made readily by forcing the member 122' into the holding portion 124j because the inclined faces 124j' are formed at the ends of the opposite sides of the holding portion 124j and the member 122' is made of a soft material. The member 122' is fully inserted into the holding portion 124j of the arm 124'' whereupon the claws 121l on the connecting side of the holding portion 124j are pierced into the member 122'. In this condition, even if a force is applied to the member 122' or the holding portion 124j of the arm 124'' in a direction to pull off the two members 122' and 124'' from each other, they are prevented from coming off from each other due to presence of the claws 124k and 124l on the holding portion 124j, which attains assured fixation between the arm 124'' and the supporting member 121'.

In this manner, with the present coupling structure, since the supporting member is held between the pair of opposite sides of the arm, similar effects to those of the fourth coupling structure shown in FIGS. 26(a) and 26(b) can be attained.

Referring now to FIGS. 29(a) and 29(b), there is shown a seventh example of coupling structure between a supporting member and an arm. The coupling structure shown includes a supporting member 131 composed of a single member 132 in a similar manner to the second to sixth examples of coupling structure described hereinabove. The member 132 has a pair of bitten portions or faces 132a and 132b, and an adhering face 132c for a film package 6. The member 132 further has a bonding agent layer 132d applied to a face thereof opposite the adhering face 132c. The coupling structure further includes an arm 134 formed as a unitary member composed of a portion 134a extending from the supporting member 131, another portion 134b contiguous to the portion 134a and extending substantially in a direction perpendicular to the portion 134a, and a plate-formed portion 134d adhered to the bonding agent layer 132d of the member 132 of the supporting member 131. It is to be noted that a portion of the arm 134 at which an indicating member is to be mounted on the arm 134 is omitted in FIGS. 29(a) and 29(b) (this also applies to the following examples of coupling structure).

With the present coupling structure, since the plate-formed portion of the arm is adhered to the side face of the supporting member, similar effects to those of the second coupling structure shown in FIG. 24 are attained, and besides such an effect can be attained that a pair of bitten faces or portions can be assured at upper and lower portions of the supporting member.

Figure 30:
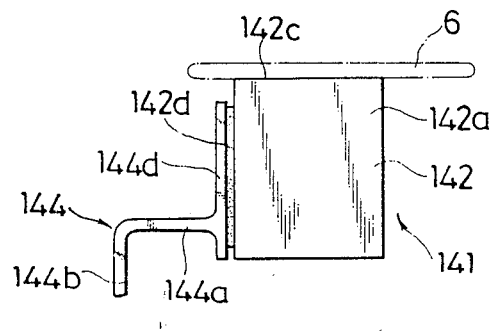

FIG. 30 shows an eighth example of coupling structure between a supporting member and an arm. Referring to FIG. 30, the coupling structure shown includes a supporting member 141 composed of a single member 142. The member 142 has a bitten portion or face 142a and another bitten portion or face not shown, and an adhering face 142c for a film package 6. The member 142 further has a bonding agent layer 142d applied to a face thereof perpendicular to the adhering face 142c. The coupling structure further includes an arm 144 formed as a unitary member composed of a portion 144a extending from the supporting member 141, another portion 144b contiguous to the portion 144a and extending substantially in a direction perpendicular to the portion 144a, and a plate-formed portion 144d adhered to the bonding agent layer 142d of the member 142 of the supporting member 141. Comparing with the seventh coupling structure shown in FIGS. 29(a) and 29(b), the present coupling structure is different in location of the face of the member 142 of the supporting member 141 to which the plate-formed portion 144d of the arm 144 is adhered. The present coupling structure thus presents similar effects to those of the seventh coupling structure.

Figure 31:
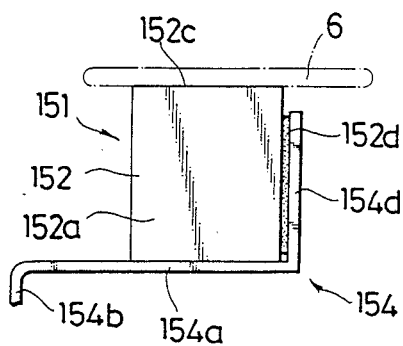

Referring now to FIG. 31, there is shown a ninth example of coupling structure between a supporting member and an arm. The coupling structure shown includes a supporting member 151 composed of a single member 152. The member 152 has a bitten portion or face 152a and another bitten portion or face not shown, and an adhering face 152c for a film package 6. The member 152 further has a bonding agent layer 152d applied to a face thereof perpendicular to the adhering face 152c. The coupling structure further includes an arm 154 formed as a unitary member composed of a portion 154a extending from the supporting member 151, another portion 154b contiguous to the portion 154a and extending substantially in a direction perpendicular to the portion 154a, and a plate-formed portion 154d adhered to the bonding agent layer 152d of the member 152 of the supporting member 151.

Comparing with the eighth coupling structure shown in FIG. 30, the present coupling structure is different in that the face of the member 152 of the supporting member 151 to which the plate-formed portion 154d of the arm 154 is decured is located at the opposite position to that in the eighth coupling structure and the portion 154a of the arm 154 extends on and across a face of the member 152 of the supporting member 151 opposite the adhering face 152c. The present coupling structure thus presents similar effects to those of the eighth coupling structure.

Referring now to FIG. 32, there is shown a tenth example of coupling structure between a supporting member and an arm. The coupling structure shown includes a supporting member 151' composed of a single member 152. The supporting member 151' is different from the supporting member 151 of the ninth coupling structure shown in FIG. 31 in that it has an additional second bonding agent layer 152d' applied to a face thereof opposing an adhering face 152c thereof. An arm 154' of the present coupling structure is also different from the arm 154 of the ninth coupling structure shown in FIG. 31 in that it has a second plate-formed portion 154d' contiguous to a first plate-formed portion 154d thereof and extending substantially in a direction perpendicular to the first plate-formed portion 154d. The second plate-formed portion 154d' of the arm 154' is adhered to the bonding agent layer 152d of the member 152 of the supporting member 151'.

With the present coupling structure, since the second plate-formed portion is adhered to the second bonding agent layer, similar effects to those of the ninth coupling structure can be attained, and besides such an effect can be anticipated that fixation between the supporting member and the arm is further assured.

Referring now to FIG. 33, there is shown an eleventh example of coupling structure between a supporting member and an arm. The coupling atructure shown includes a supporting member 161 composed of a single member 162 having a bitten portion or face 162a. The member 162 further has a bonding agent layer 162d applied to a side face thereof. An arm 164 of the coupling structure is composed of a portion 164a extending from the supporting member 161, another portion 164b contiguous to the portion 164a and extending substantially in a direction perpendicular to the portion 164a, a plate-formed portion 164d adhered to the bonding agent layer 162d of the supporting member 161, and a bonding agent layer 164e applied to the plate-formed portion 164d. A film package 6 is adapted to be applied to the bonding agent layer 164e of the arm 164. The present coupling structure also presents similar effects to those of the seventh coupling structure shown in FIGS. 29(a) and 29(b).

It is to be noted that, while in any of the first to eleventh coupling structures two portions interconnecting the opposite end portions of the arm are described each in the form of a bar-like member having a rectangular cross section, they need not have such a specific cross section and may have some other cross section such as, for example, an X-shaped cross section so that they may have an increased strength. Further, the material of the arm is not limited to a synthetic resing and may otherwise be a metal or some other suitable material.

In the following, an example of structure for supporting a film package on a supporting member will be described with reference to FIGS. 34(a) and 34(d). A film package 6 is enclosed in an envelope 6'. The envelope 6' is made of a softer material than that of an outer package member or cover of the film package 6. Such an outer package member of the film package 6 is limited in flexibility due to the necessity for interruption of light and also for protection of an X-ray film. Therefore, when the film package 6 is inserted into an oral cavity, it will in most cases give a disagreeable feeling to the patient due to lack in flexibility. Besides, upon X-ray photographing, saliva will always apply to the film package 6. Upon processing after such photographing, the saliva on the film package 6 may apply to the dentist, which will give a disagreeable feeling to the dentist and besides is not preferable for sanitation. From those reasons, in most cases a film package 6 is enclosed in an envelope 6' made of a very flexible material and inserted in this condition into an oral cavity of a patient.

A bonding agent layer 170 is applied to an adhering portion or face 12 of a supporting member 11. A supporting element 171 for supporting an envelope 6' and a film package 6 in the envelope 6' thereon is formed separately from the supporting member 11 and applied to the bonding agent layer 170 of the supporting member 11. The supporting element 171 is composed of a U-shaped member 171a made of a synthetic resin having a suitable elasticity. The U-shaped member 171a has a wall 171b adapted to be applied to the bonding agent layer 170 of the supporting member 11, and a supporting portion 171c for cooperating with the wall 171b to hold therebetween an envelope 6' and a film package 6 in the envelope 6'.

When X-ray photographing is to be conducted using a film package 6 enclosed in an enveloped 6', the wall 171b of the supporting element 171 is applied to the adhering portion 12 of the arm 11 to which the film package 6 is to be primarily adhered. Consequently, the supporting element 171 is secured to the supporting member 11. The envelope 6' in which the film package 6 is enclosed is subsequently inserted into the supporting portion 171c of the supporting element 171. Since the U-shaped member 171a of the supporting element 171 has a suitable elasticity, the envelope 6' inserted in this manner is held firmly by the supporting portion 171c of the supporting element 171 so that the film package 6 is supported with certainty on the supporting element 171.

If such a flexible envelope 6' is otherwise applied directly to the adhering portion 12 of the supporting member 11, it is impossible to support the film package 6 in the flexible envelope 6' at a fixed location. To the contrary, in the case of the present structure in which the supporting element 171 is used, while the film package 6 is enclosed in the envelope 6', it is supported fixedly on the supporting member 11 in a similar condition as it is applied directly to the adhering portion 12 of the supporting member 11. Accordingly, X-ray photographing can be conducted without any trouble.

It is to be noted that while in the supporting structure the supporting element is described composed of a U-shaped member, it may have any other configuration only if a film package or an envelope enclosed in an envelope can be fixed firmly thereto. Further, while the supporting member and the arm are shown formed as a unitary member, they may otherwise be formed as separate members. Meanwhile, naturally a film package 6 may otherwise be adhered directly to the supporting element 171.

Various embodiments of the present invention have been described so far. While in any of the embodiments coupling between an end portion of an arm and a mounting member is described provided by a projection and a hole for receiving the projection therein, it may be provided by any other means. Further, while an indicating member is described formed either as a ring or as a substantially circular plate member, it is not limited to the specific members and may be a member of any other configuration only if it is made of a material which transmits an X-ray therethrough. For example, plate members of various configurations, plate members in which openings of various shapes are formed and cross-shaped bar members may be used for the indicating member.

As apparent from the foregoing description, according to the present invention, a dental X-ray irradiation indicating device comprises a supporting member, an arm means extending from the supporting member, and an indicating member mounted on the arm means by way of a mounting member, whereby the indicating member is positioned in an opposing relationship to an intra-oral X-ray film package which is held in a predetermined angular position in an oral cavity of a patient. Therefore, it is only necessary to irradiate an X-ray with reference to the indicating member. Accordingly, irradiation of an X-ray can be effected readily and accurately with a simple construction. Besides, an X-ray image of an object of photographing can be obtained with a substantially same size on an X-ray film.

What is claimed is:

1. A dental X-ray irradiation indicating device for holding an intra-oral X-ray film package in an oral cavity of a patient and for indicating a direction in which an X-ray is to be irradiated from outside the oral cavity, comprising a supporting member having a film fixing portion to which an intra-oral X-ray film package is to be fixed and a bitten portion means for being bitten by a tooth, an arm means which extends outwardly of an oral cavity from said supporting member when said bitten portion means of said supporting member is bitten by a tooth, an indexing means for defining an inclined plane and indicating a direction perpendicular to the inclined plane in which an X-ray is to be irradiated, said indexing means including a first indexing element defining a first plane, a second indexing element defining the inclined plane which is inclined by a predetermined angle with respect to the first plane, and a connecting element for interconnecting said first and second indexing elements, and a mounting structure for removably mounting said indexing means on said arm means.

2. A dental X-ray irradiation indicating device as claimed in claim 1, wherein said indexing means has a ring-like configuration.

3. A dental X-ray irradiation indicating device as claimed in claim 1, wherein said first and second indexing elements are complementary half circles of a circular ring.

4. A dental X-ray irradiation indicating device as claimed in claim 1, wherein said mounting structure includes a pair of mounting elements secured to opposite sides of one of said first and second indexing elements.

5. A dental X-ray irradiation indicating device as claimed in claim 1, wherein said mounting structure has a through-hole formed therein for receiving part of said arm means therein.

6. A dental X-ray irradiation indicating device as claimed in claim 5, wherein said through-hole has a central axis extending in a direction perpendicular the first plane.

7. A dental X-ray irradiation indicating device as claimed in claim 1, wherein said mounting structure includes a pair of guides secured to opposite sides of one of said first and second indexing elements, and a mounting member mounted for sliding movement on each of said guides.

8. A dental X-ray irradiation indicating device as claimed in claim 1, wherein said mounting structure includes a pair of pivotal members mounted for pivotal motion on opposite sides of one of said first and second indexing elements, and a mounting member secured to each of said pivotal members.

9. A dental X-ray irradiation indicating device as claimed in claim 1, wherein said connecting element is connected for pivotal motion to said first indexing element by means of a fastening member.

10. A dental X-ray irradiation indicating device as claimed in claim 9, wherein said fastening member is a screw.

11. A dental X-ray irradiation indicating device as claimed in claim 9, wherein said connecting element and said first indexing element have mutually cooperating graduations applied thereto.

12. A dental X-ray irradiation indicating device as claimed in claim 1, wherein said arm means has a flat adhering face means for being adhered to a face of said supporting member.

13. A dental X-ray irradiation indicating device as claimed in claim 1, wherein said arm means has a flat adhering face means for being adhered to said supporting member, and a holding portion means for holding the intra-oral X-ray film package.

14. A dental X-ray irradiation indicating device as claimed in claim 1, wherein said arm means has a piercing portion means for being pierced into said supporting member.

15. A dental X-ray irradiation indicating device as claimed in claim 14, wherein said piercing portion means of said arm means has a claw for preventing said arm means from coming off from said supporting member.

16. A dental X-ray irradiation indicating device as claimed in claim 1, wherein said arm means has a holding portion for holding the opposite sides of said supporting member.

17. A dental X-ray irradiation indicating device as claimed in claim 16, wherein said holding portion has a claw formed thereon for preventing said arm means from coming off from said supporting member.

18. A dental X-ray irradiation indicating device for holding an intra-oral X-ray film package in an oral cavity of a patient and for indicating a direction in which an X-ray is to be irradiated from outside the oral cavity, comprising a supporting member having a film fixing portion to which an intra-oral X-ray film package is to be fixed and a bitten portion means for being bitten by a tooth, an arm means which extends outwardly of an oral cavity from said supporting member when said bitten portion means of said supporting member is bitten by a tooth, an indexing means for defining a plurality of inclined planes at different angular positions of inclination and indicating a direction perpendicular to each said inclined plane in which an X-ray is to be irradiated, and a mounting structure provided on said indexing means for selectively engaging said arm means at plural positions of engagment and for removably and selectively mounting said indexing means at different angular positions for defining said plurality of inclined planes on said arm means.

19. A dental X-ray irradiation indicating device as claimed in claim 18, wherein said mounting structure includes a plurality of mounting members secured to a periphery of said indexing means in different orientations from each other with respect to said arm means.

20. A dental X-ray irradiation indicating device as claimed in claim 18, wherein said mounting structure includes a block having a plurality of mounting elements provided in a juxtaposed relationship therein for engaging with said arm means in different orientations from each other.

21. A dental X-ray irradiation indicating device as claimed in claim 18, wherein said mounting structure includes a fixing member secured to said indexing means, a single mounting member for engaging with said arm means, and a plurality of engaging means coupled to said mounting member for engaging with said fixing member in different orientations from each other.

22. A dental X-ray irradiation indicating device as claimed in claim 18, wherein said arm means has a flat adhering face means for being adhered to a face of said supporting member.

23. A dental X-ray irradiation indicating device as claimed in claim 18, wherein said arm means has a flat adhering face means for being adhered to said supporting member, and a holding portion means for holding the intra-oral X-ray film package.

24. A dental X-ray irradiation indicating device for holding an intra-oral X-ray film package in an oral cavity of a patient and for indicating a direction in which an X-ray is to be irradiated from outside the oral cavity, comprising a supporting member having a film fixing portion to which an intra-oral X-ray film package is to be fixed and a bitten portion means for being bitten by a tooth, an arm means which extends outwardly of an oral cavity from said supporting member when said bitten portion means of said supporting member is bitten by a tooth, an indexing means for defining an inclined plane and indicating a direction perpendicular to the inclined plane in which an X-ray is to be irradiated, and a mounting structure provided on said indexing means for selectively engaging said arm means at plural positions of engagement and for removably and selectively mounting said indexing means at different angular positions for defining said inclined plane on said arm means; wherein said mounting structure includes a non-linear guide secured to said indexing means, and a single mounting member mounted for movement on said guide for engaging with said arm means.

25. A dental X-ray irradiation indicating device for holding an intra-oral X-ray film package in an oral cavity of a patient and for indicating a direction in which an X-ray is to be irradiated from outside the oral cavity, comprising a supporting member having a film fixing portion to which an intra-oral X-ray film package is to be fixed and a bitten portion means for being bitten by a tooth, an arm means which extends outwardly of an oral cavity from said supporting member when said bitten portion means of said supporting member is bitten by a tooth, an indexing means for defining an inclined plane and indicating a direction perpendicular to the inclined plane in which an X-ray is to be irradiated, and a mounting structure provided on said indexing means for selectively engaging said arm means at plural positions of engagement and for removably and selectively mounting said indexing means at different angular positions for defining said inclined plane on said arm means, wherein said arm means has a piercing portion means for being pierced into said supporting member.

26. A dental X-ray irradiation indicating device as claimed in claim 25, wherein said piercing portion means of said arm means has a claw for preventing said arm means from coming off from said supporting member.

27. A dental X-ray irradiation indicating device for holding an intra-oral X-ray film package in an oral cavity of a patient and for indicating a direction in which an X-ray is to be irradiated from outside the oral cavity, comprising a supporting member having a film fixing portion to which an intra-oral X-ray film package is to be fixed and a bitten portion means for being bitten by a tooth, an arm means which extends outwardly of an oral cavity from said supporting member when said bitten portion means of said supporting member is bitten by a tooth, an indexing means for defining an inclined plane and indicating a direction perpendicular to the inclined plane in which an X-ray is to be irradiated, and a mounting structure provided on said indexing means for selectively engaging said arm means at plural positions of engagement and for removably and selectively mounting said indexing means at different angular positions for defining said inclined plane on said arm means, wherein said arms means has a holding portion for holding opposite sides of said supporting member.

28. A dental X-ray irradiation indicating device as claimed in claim 27, wherein said holding portion has a claw formed thereon for preventing said arm means from coming off from said supporting member.

29. A dental X-ray irradiation indicating device for holding an intra-oral X-ray film package in an oral cavity of a patient and for indicating a direction in which an X-ray is to be irradiated from outside the oral cavity, comprising a supporting member having a film fixing portion to which an intra-oral X-ray film package is to be fixed and a bitten portion for being bitten by a tooth, an arm means which extends outwardly of an oral cavity from said supporting member when said bitten portion of said supporting member is bitten by a tooth, said arm means having a holding portion for holding opposite sides of said supporting member, said holding portion having a claw piercing formed thereon for preventing said arm means from coming off from said supporting member, and an indexing means for indicating a direction in which X-ray is to be irradiated, said indexing means having a single mounting member at which said indexing means is to be mounted on said arm means, said indexing means being disposed in a predetermined angular position with respect to a plane of the intra-oral X-ray film package held in position in the oral cavity.

30. A dental X-ray irradiation indicating device for holding an intra-oral X-ray film package in an oral cavity of a patient and for indicating a direction in which an X-ray is to be irradiated from outside the oral cavity, comprising a supporting member having a film fixing portion to which an intra-oral X-ray film package is to be fixed and a bitten portion for being bitten by a tooth, an arm means which extends outwardly of an oral cavity from said supporting member when said bitten portion of said supporting member is bitten by a tooth, said arm means having a piercing portion for being pierced into said supporting member, said piercing portion of said arm means having a claw for preventing said arm means from coming off from said supporting member, and an indexing means for indicating a direction in which an X-ray is to be irradiated, said indexing means having a single mounting member at which said indexing means is to be mounted on said arm means, said indexing means being disposed in a predetermined angular position with respect to a plane of the intra-oral X-ray film package held in position in the oral cavity.

31. A dental X-ray irradiation indicating device for holding an intra-oral X-ray film package in an oral cavity of a patient and for indicating a direction in which an X-ray is to be irradiated from outside the oral cavity, comprising a supporting member having an adhering portion to which a layer of a bonding agent is to be applied and a bitten portion for being bitten by a tooth, an arm means which extends outwardly of an oral cavity from said supporting member when said bitten portion is held in position in the oral cavity, an indexing means removably mounted at a predetermined location on said arm means for indicating a direction in which an X-ray is to be irradiated, said indexing means being disposed in a predetermined angular position with respect to a plane of an intra-oral X-ray film package held in position in the oral cavity, and a support element having an adhering face for being adhered to said adhering portion of said supporting member and a supporting portion for supporting an intra-oral X-ray film package thereon.

32. A dental X-ray irradiation indicating device as claimed in claim 31, wherein said support element is a holding member having a U-shaped cross section.

* * * * *